USOO5766593A

United States Patent [19]
Lichenstein et al.

[11] Patent Number: 5,766,593
[45] Date of Patent: Jun. 16, 1998

[54] ANTI-INFLAMMATORY CD14 PEPTIDES

[75] Inventors: Henri S. Lichenstein, Ventura, Calif.; Samuel D. Wright, Larchmont, N.Y.; Linda O. Narhi, Camarillo; Shao-Chieh Juan, Moorpark, both of Calif.

[73] Assignee: Amgen Inc., Thousand Oaks, Calif.

[21] Appl. No.: 366,953

[22] Filed: Dec. 30, 1994

[51] Int. Cl.$^6$ .......................... A61K 38/00; C07K 14/705
[52] U.S. Cl. ........................... 424/185.1; 424/198.1; 424/278.1; 514/2; 514/9; 514/12; 514/16; 530/300; 530/317; 530/324; 530/328
[58] Field of Search ........................... 530/300, 395, 530/317, 324, 388; 424/185.1, 198.1, 278.1; 514/2, 9, 12, 16

[56] References Cited

FOREIGN PATENT DOCUMENTS

| | | | |
|---|---|---|---|
| WO 91/01639 | 2/1991 | WIPO . | |
| WO 92/04908 | 4/1992 | WIPO . | |
| WO 93/19772 | 10/1993 | WIPO . | |
| 96/08272 | 3/1996 | WIPO | A61K 39/40 |

OTHER PUBLICATIONS

Ferrero et al. (1990) *The Journal of Immunology* 145:331–336.
Ferrero et al. (1988) *Nucleic Acids Research* 16:9.
Goyert et al. (1988) *Science* 239:497–500.
Juan et al. (1995) *The Journal of Biological Chemistry* 270: 1382–1387.
Pugin et al. (1994) *Immunity* 1:509–516.
Setoguchi et al. (1989) *Biochimica et Biophysica Acta*. 1008:213–222.
Viriyakosol et al. (1995) *The Journal of Biological Chemistry* 270:331–368.
Juan et al. (1995). 'Identification of a lipopolysaccharide binding domain in CD14 between amino acids 57 and 64', *J. Bio Chem* 270(10):5219–5224.
Juan et al. (1995). 'Identification of a domain in sCD14 essential for Lipopolysaccharide (LPS)signaling but not LPS binding'. *J Bio Chem* 270(29):17237–17242.
McGinley et al. (1950. 'CD14: Physical properties and identification of an exposed site that is protected by Lipopolysaccharide', *J Bio Chem* 270(10):5213–5218.
Weinstein (1983). 'Chemistry and Biochemistry of Amino Acids, Peptides and Proteins', Marcel Dekker, Inc. 7:336–345.

*Primary Examiner*—Thomas M. Cunningham
*Attorney, Agent, or Firm*—Daniel R. Curry; Robert R. Cook; Steven M. Odre

[57] ABSTRACT

The invention relates to anti-inflammatory peptides that are based on peptide regions 7–10, 11–14, and 57–64 of CD14.

17 Claims, 17 Drawing Sheets

| sCD14 Mutant | | Amino Acid Sequence |
|---|---|---|
| sCD14$_{1-348}$ | (SEQ ID NO: 28) | rvdadadprqyadtvk |
| SCD14$_{D59A}$ | (SEQ ID NO: 29) | rvdadaAprqyadtvk |
| SCD14$_{P60A}$ | (SEQ ID NO: 30) | rvdadadArqyadtvk |
| SCD14$_{R61A}$ | (SEQ ID NO: 31) | rvdadadpAqyadtvk |
| SCD14$_{Q62A}$ | (SEQ ID NO: 32) | rvdadadprAyadtvk |
| SCD14$_{Y63A}$ | (SEQ ID NO: 33) | rvdadadprqAadtvk |
| SCD14$_{D65A}$ | (SEQ ID NO: 34) | rvdadadprqyaAtvk |
| SCD14$_{(59-65)A}$ | (SEQ ID NO: 35) | rvdadaAAAAAaAtvk |

FIG. 8

```
(SEQ ID NO: 36)       TTPEPCELDD EDFRCVCNFS EPQPDWSEAF QCVSAVEVEI HAGGLNLEPF LKRVD 1. sCD14(7-10)A       -----AAAA- ---------- ---------- ---------- ---------- -----
2. sCD14(11-14)A      ---------- AAAA------ ---------- ---------- ---------- -----
3. sCD14(18-21)A      ---------- -------AAA A--------- ---------- ---------- -----
4. sCD14(22-25)A      ---------- ---------- -AAAA----- ---------- ---------- -----
5. sCD14(26-28)A      ---------- ---------- -----AAA-- ---------- ---------- -----
6. sCD14(29-31)A      ---------- ---------- --------AA A--------- ---------- -----
7. sCD14(45-48)A      ---------- ---------- ---------- ---------- ----AAAA-- -----
8. sCD14(49-52)A      ---------- ---------- ---------- ---------- --------AA AA---
```

ANTI-INFLAMMATORY CD14 PEPTIDES

FIELD OF THE INVENTION

Generally, the invention relates to the field of peptides that have anti-inflammatory properties. These peptides were designed based on amino acids 57 to 64, 7 to 10 and 11 to 14, inclusive, of the cell-surface antigen CD14. Amino acids 57 to 64 of CD14 were found to correspond to the binding domain of CD14 to lipopolysacharride (LPS, also referred to as endotoxin). Amino acids 7 to 10 and 11 to 14 of CD14 were found to be an important CD14 domain for inflammatory responses in cells, including IL-6 production. The peptides of the invention may be used to treat inflammatory conditions, such as sepsis, and to detect LPS in samples.

BACKGROUND OF THE INVENTION

Sepsis is a life-threatening medical condition that can be brought on by infection or trauma. The symptoms of sepsis can include chills, profuse sweating, fever, weakness, or hypotension, followed by leukopenia, intravascular coagulation, shock, adult respiratory distress syndrome, multiple organ failure, and often, death. R. Ulevitch, et al., *J. Trauma* 30: S189–92 (1990).

The symptoms of sepsis can be induced by certain released microbes during infection or trauma. Some pathogenic bacteria, viruses, and plants produce such sepsis-inducing substances.

The lipopolysaccharides ("LPS"; also, "endotoxins") that are typically present on the outer membrane of all gram-negative bacteria are among the most studied and best understood sepsis-inducing substances. While the precise chemical structures of LPS molecules obtained from different bacteria may vary in a species-specific fashion, a region called the lipid A region is common to all LPS molecules. E. Rietschel et al., in *Handbook of Endotoxins*, 1: 187–214, eds. R. Proctor and E. Rietschel, Elsevier, Amsterdam (1984). This lipid A region is responsible for many, if not all, of the LPS-dependent pathophysiologic changes that characterize sepsis.

LPS is believed to be a primary cause of death in humans afflicted with gram-negative sepsis. van Deventer et al., *Lancet*, 1: 605 (1988); Ziegler et al., *J. Infect. Dis.*, 136: 19–28 (1987). Treatment of patients suffering from sepsis and gram-negative bacteraemia with a monoclonal antibody against LPS decreased their mortality rate. Ziegler et al., *N. Eng. J. Med.*, 324: 429 (1991).

Sepsis is also caused by gram-positive bacteria. Bone, R. C. Arch. Intern. Med., 154: 26–34 (1994). The activation of host cells can originate from gram-positive cell walls or purified cell components such as peptidoglycan and lipoteichoic acid. Such substances induce a similar pattern of inflammatory responses to those induced by LPS. Chin and Kostura, *J. Immunol.* 151: 5574–5585 (1993); Mattson et al., *FEMS Immun. Med. Microbiol.* 7: 281–288 (1993); and Rotta, *J. Z. Immunol. Forsch. Bd.:* 149: 230–244 (1975).).

LPS and gram-positive cell wall substances cause polymorphonuclear leukocytes, endothelial cells, and cells of the monocyte/macrophage lineage to rapidly produce and release a variety of cell products, including cytokines, which are capable of initiating, modulating or mediating humoral and cellular immune responses and processes.

One particular cytokine, alpha-cachectin or tumor necrosis factor (TNF), is apparently a primary mediator of septic shock. Beutler et al., *N. Eng. J. Med.*, 316: 379 (1987). Intravenous injection of LPS into experimental animals and man produces a rapid, transient release of TNF. Beutler et al., *J. Immunol.*, 135: 3972 (1985); Mathison et al., *J. Clin. Invest.* 81: 1925 (1988). Pretreatment of animals with anti-TNF antibodies can modulate septic shock. Beutler et al., *Science*, 229: 869, (1985); Mathison et al., *J. Clin. Invest.* 81: 1925 (1988).

Molecular receptors that can combine with sepsis inducing substances, and that once combined, initiate certain chemical reactions, play a critical role in the etiology of the symptoms of sepsis. CD14 is a 55-kD glycoprotein expressed strongly on the surface of monocytes and macrophages, and weakly on the surface of granulocytes, such as neutrophils. S. M. Goyert et al., *J. Immunol.* 137: 3909 (1986). A. Haziot et al., *J. Immunol.* 141: 547–552 (1988); S. M. Goyert et al., *Science* 239: 497 (1988). CD14 is linked by a cleavable glycosyl phosphatidyl inositol tail [A. Haziot et al., *J. Immunol.* 141: 547–552 (1988)] to the exoplasmic surface of mature monocytes, macrophages, granulocytes and dendritic reticulum cells, or renal non-glomerular endothelium, and of hepatocytes in rejected livers. A soluble form of CD14 is present in normal sera and in the urine of nephrotic patients. Bazil et al., *Eur. J. Immunol.* 16: 1583 (1986).

CD14 plays a crucial role in mediating responses of cells to LPS. Treatment of monocytes (Wright, S. D., et al., *Science* 90: 1431–1433 (1990)) or PMN (Wright, S. D., et al., *J. Exp. Med.* 173: 1281–1286 (1991)) with monoclonal antibodies against CD14 blocks their responses to LPS. Several cell types, such as endothelial cells and astrocytes, respond to LPS but do not express CD14. These cells nevertheless require CD14, and sCD14 from the plasma mediates this response (Frey, E. A., et al., *J. Exp. Med.* 176: 1665–1671 (1992)). These observations have been confirmed with a wide number of cell types and animal species, and have been confirmed with assays of a large variety of in vitro responses to LPS. Importantly, animals injected with anti-CD14 become hyporesponsive to LPS and mice lacking CD14 fail to respond to LPS.

CD14 mediates responses by binding to LPS. Complexes of LPS and sCD14 exhibit a 1:1 stoichiometry (Hailman, E., et al., *J. Exp. Med.* 179: 269–277 (1994)), and these complexes initiate TNF production in monocytes (Dentener, M. A., et al., *J. Immunol.* 7: 2885–2891 (1993)), IL-6 production in astrocytes (Frey, E., et al., *Ibid.* (1992)), production of adhesion molecules in endothelial cells (Frey, E., et al., *Ibid.* (1992)) and activation of leukocyte integrins in PMN (Hailman, E., et al., *Ibid.* (1994)). Spontaneous binding of LPS to CD14 is slow, but this binding may be dramatically accelerated by lipopolysaccharide binding protein LBP. LBP acts in a catalytic fashion, with one molecule of LBP transferring hundreds of LPS molecules to hundreds of CD14 molecules.

Other experiments have shown that cell activation can also be induced by interaction of CD14 with components of gram-positive bacteria such as *B. subtilis, S. aureus,* and *S. mitus* (Pugin et al., *Immunity* 1: 509–516 (1994). Furthermore, interaction of CD14 with lipoarabinomannan from the cell wall of *Mycobacterium tuberculosis* also induces cellular activation in a CD14 dependent fashion (Zhang et al., *J. Clin. Invest.* 91: 2076–2083 (1993); Pugin et al., *Immunity* 1: 509–516 (1994)). These studies suggest that CD14 is a receptor which recognizes a wide variety of bacterial structures. Interaction of CD14 with these structures initiates host inflammatory responses.

From the preceding background, it is evident that preventing interaction of CD14 with microbial structures could reduce inflammatory responses in leukocytes, endothelial and epithelial cells. Indeed, neutralizing mAbs to CD14 antagonize cellular responses to LPS, lipoarabinomannan and gram-positive cell wall components in vitro (Pugin et al., *Immunity* 1: 509–516 (1994)) and recent reports have shown that CD14 mAbs are also effective in vivo. These observations suggest that CD14 may be an important pharmacologic target for diseases mediated by LPS, lipoarabinomannan and gram-positive bacterial components.

The cDNAs and the genes for human and murine CD14 have been cloned and sequenced. E. Ferrero and S. M. Goyert, *Nuc. Acids Res.* 16: 4173 (1988); S. M. Goyert et al., *Science* 239: 497 (1988); M. Setoguchi et al., *Biochem. Biophys. Acta* 1008: 213–22 (1989). The sequence analysis revealed that CD14 belongs to a family of leucine-rich membrane-bound and soluble proteins that have receptor and cell adhesive functions. M. Setoguchi et al., *Biochem. Biophys. Acta* 1008: 213–22 (1989); E. Ferrero, et al., *J. Immunol.* 145: 133 (1990).

The human CD14 protein sequence contains five potential sites for N-linked glycosylation and contains a 10 fold repeat of a leucine rich motif (LXXLXLX). There is a 66% amino acid sequence identity between the murine and human CD14s.

In situ chromosomal hybridization of the $^3$H-labeled cDNA probe to normal human metaphase cells resulted in specific labeling only of chromosome 5. S.M. Goyert et al., *Science* 239: 497 (1988). The labeled sites were clustered at regions 5q22–q32 of this chromosome. The largest cluster of grains was located at 5q23–q31. S. M. Goyert et al., *Science* 239: 497 (1988). This region of human chromosome 5 is known to contain a cluster of genes that encode several myeloid-specific growth factors or growth factor receptors, as well as other growth factor and receptor genes. S. M. Goyert et al., *Science* 239: 497 (1988). The mapping of the CD14 gene to this region of chromosome 5, its expression preferentially by mature myeloid cells, and its deletion in the malignant cells of patients having myeloid leukemias and del(5q) suggest that the CD14 antigen may play a role in the pathogenesis of myeloid disorders.

The murine gene is located on mouse chromosome 18, which like the human gene also contains at least five genes encoding receptors. M. Setoguchi, H. Nasu, S. Yoshida, Y. Higuchi, S. Akizuki, and S. Yamamoto, *Biochem. Biophys. Acta* 1008: 213–22 (1989); E. Ferrero, C. L. Hsieh, U. Francke and S. M. Goyert, *J. Immunol.* 145: 133 (1990).

For the preceding reasons, it is an object of this invention to develop methods and therapies for the effective treatment, including prevention, for symptoms of inflammatory conditions, including sepsis. It is also an object of this invention to develop methods and therapies for the effective protection of individuals who are at risk of becoming afflicted by the symptoms of inflammation, including sepsis.

It is another object of this invention to develop methods and therapies for the effective treatment, including prevention, of symptoms of diseases that are mediated by LPS, gram-negative bacteraemia, gram-positive cell components, gram-positive bacteraemia, mycobacterial lipoarabinomannan, mycobacterial infections and/or CD14. Such diseases include ARDS, acute pancreatitis, acute and chronic liver failure, intestinal or liver transplantation, inflammatory bowel disease, graft vs. host disease in bone marrow transplantation and tuberculosis.

SUMMARY OF THE INVENTION

The present inventors have discovered a first group of peptides that are capable of binding to lipopolysaccharide, resulting in inhibition of the binding of LPS or gram-positive cell components to CD14, thus reducing or eliminating CD14 mediated inflammatory responses. As used herein, inhibition of binding of LPS also means inhibition of binding of gram-positive cell components. This first group of peptides was designed by the inventors based on their important discovery, disclosed herein, of an LPS-binding domain in CD14 to LPS. This first group of peptides is capable of binding to LPS thereby preventing further binding of microbial cell components to CD14. If microbial cell interaction with CD14 is prevented, the cascade of events leading to inflammation, and especially sepsis, are reduced or prevented. Therefore, the peptides of this invention have anti-inflammatory properties.

A second group of peptides is expected to be capable of preventing LPS (or gram positive cell components) stimulation of inflammatory responses, such as IL-6 production. These peptides were designed based on the discovery that there are two additional important peptide regions in CD14: amino acids 7 to 10 and 11 to 14. The evidence provided herein shows, inter alia, that a CD14 mutant having the region from amino acids 7 to 10 in CD14 replaced with alanine residues mediates substantially reduced cellular production of the inflammatory cytokine IL-6 in response to LPS, as compared to native CD14 (See Example 10). Moreover, the regions 7–10 and 11–14 in CD14 are recognized by the neutralizing anti-CD14 antibody 3C10 (See Example 9).

The first group of peptides of the present invention may be linear or cyclic. The linear first group peptides of this invention comprise the following amino acid sequence:

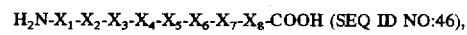

H$_2$N-X$_1$-X$_2$-X$_3$-X$_4$-X$_5$-X$_6$-X$_7$-X$_8$-COOH (SEQ ID NO:46), wherein, X$_1$ is selected from the group consisting of Asp and Glu;

X$_2$ is selected from the group consisting of Ala and Ser;

X$_3$ is selected from the group consisting of Asp and Glu;

X$_4$ is selected from the group consisting of Pro and Gly;

X$_5$ is selected from the group consisting of Arg and Lys;

X$_6$ is selected from the group consisting of Gln, Asn and His;

X$_7$ is selected from the group consisting of Tyr, Trp and Phe;

X$_8$ is selected from the group consisting of Ala and Ser; and physiologically acceptable salts thereof; and further wherein said peptide binds to lipopolysaccharide.

A particularly preferred linear peptide is:

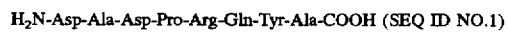

H$_2$N-Asp-Ala-Asp-Pro-Arg-Gln-Tyr-Ala-COOH (SEQ ID NO.1)

which corresponds to amino acids 57–64 of native human CD14. These are the amino acids in CD14 primarily involved in binding to LPS.

The cyclic first group peptides of this invention comprise any of the following amino acid sequences:

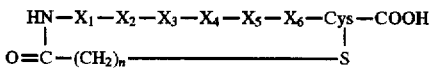

$$\begin{array}{l}\text{HN}-\text{X}_1-\text{X}_2-\text{X}_3-\text{X}_4-\text{X}_5-\text{X}_6-\text{Cys}-\text{COOH}\\ |\qquad\qquad\qquad\qquad\qquad\qquad\quad|\\ \text{O}=\text{C}-(\text{CH}_2)_n\text{———————————S}\end{array}$$

wherein,

X$_1$ is selected from the group consisting of Asp and Glu;

X$_2$ is selected from the group consisting of Pro and Gly;

$X_3$ is selected from the group consisting of Arg and Lys;

$X_4$ is selected from the group consisting of Gln, Asn and His;

$X_5$ is selected from the group consisting of Tyr, Trp and Phe;

$X_6$ is selected from the group consisting of Ala and Ser;

n is from 1 to 3; and physiologically acceptable salts thereof; and further wherein said peptide binds to lipopolysaccharide.

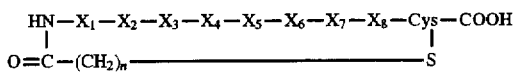

wherein, $X_1$ is selected from the group consisting of Ala and Ser;
$X_2$ is selected from the group consisting of Asp and Glu;
$X_3$ is selected from the group consisting of Pro and Gly;
$X_4$ is selected from the group consisting of Arg and Lys;
$X_5$ is selected from the group consisting of Gln, Asn and His;
$X_6$ is selected from the group consisting of Tyr, Trp and Phe;
$X_7$ is selected from the group consisting of Ala and Ser;
$X_8$ is selected from the group consisting of Asp and Glu;
n is from 1 to 3; and physiologically acceptable salts thereof; and further wherein said peptide binds to lipopolysaccharide.

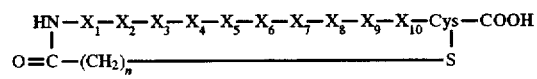

wherein, $X_1$ is selected from the group consisting of Asp and Glu;
$X_2$ is selected from the group consisting of Ala and Ser;
$X_3$ is selected from the group consisting of Asp and Glu;
$X_4$ is selected from the group consisting of Pro and Gly;
$X_5$ is selected from the group consisting of Arg and Lys;
$X_6$ is selected from the group consisting of Gln, Asn and His;
$X_7$ is selected from the group consisting of Tyr, Trp and Phe;
$X_8$ is selected from the group consisting of Ala and Ser;
$X_9$ is selected from the group consisting of Asp and Glu;
$X_{10}$ is selected from the group consisting of Thr and Ser;
n is from 1 to 3; and physiologically acceptable salts thereof; and further wherein said peptide binds to lipopolysaccharide.

Specifically preferred cyclic first group peptides are the following:

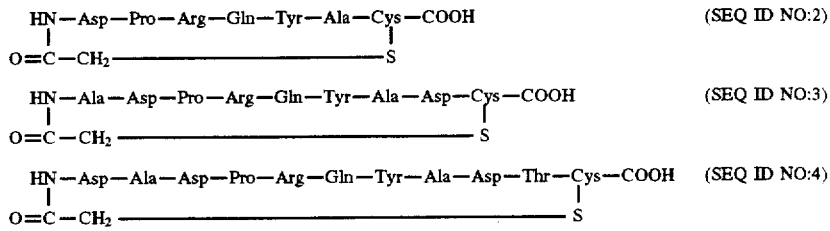

and, in each case, physiologically acceptable salts thereof.

The second group of peptides comprises the following amino acid sequences:

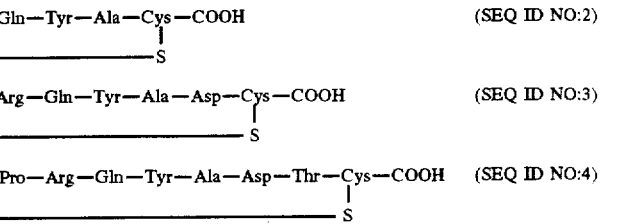

wherein n is from 1 to 3 (preferably 1); or

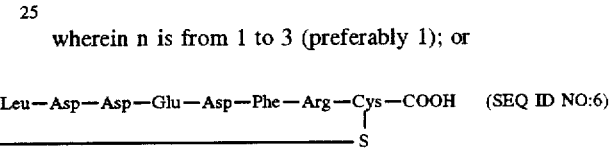

and, in each case, physiologically acceptable salts thereof.

The peptides of this invention may be prepared by (a) standard synthetic methods, (b) derivation from CD14, (c) recombinant methods, (d) a combination of one or more of (a)–(c), or other methods of preparing peptides.

The peptides of this invention may be used for therapeutic or prophylactic purposes by incorporating them into appropriate pharmaceutical carrier materials and administering an effective amount to a patient, such as a human (or other mammal) in need thereof.

Since the peptides of this invention are capable of binding to LPS or gram-positive cell components, they may also be bound to a support material and used to remove LPS or gram-positive cell components from a sample, such as a body fluid. Further, in labeled form they may be used to detect and/or quantitate LPS or gram-positive cell components in a sample, such as a body fluid. Accordingly, kits containing one or more of these peptides may be supplied for diagnostic or purification purposes.

The invention also relates to antibodies, including monoclonal antibodies, to the peptides of this invention, and to hybridoma cell lines that produce the monoclonal antibodies. Since the antibodies bind to the domain of CD14 that enables binding of CD14 to LPS or gram-positive cell components, the antibodies inhibit or prevent binding of cell-bound CD14 to LPS or gram-positive cell components and hence, are useful to treat inflammatory conditions. Such antibodies may also be used to detect and/or quantitate LPS or gram positive cell components in a sample, such as a body fluid.

BRIEF DESCRIPTION OF THE FIGURES

Numerous other aspects and advantages of the present invention will therefore be apparent upon consideration of the following detailed description thereof, reference being made to the drawings wherein:

FIG. 8 is a summary of amino acid changes engineered between amino acids 59–65 of sCD14. Mutant sCD14 proteins are designated as sCD14$_{X\#A}$ where X denotes wild-type amino acid residue at position # which has been changed to A (Ala). sCD14$_{(59\text{-}65)A}$ contains all alanines from position 59 through 65. Sequences between amino acid 53 and 68 of each mutant protein is shown. Bold-faced, large-capitalized sequences indicate mutated residues.

FIG. 11 shows sequences of the site-directed mutants of sCD14 for 3C10 epitope mapping studies. The first sequence indicates the wildtype sCD14 sequence from amino acid residues 1 to 55 of the mature protein. Hyphens in the mutant sCD14 sequences indicate the same amino acid sequence as wildtype sequences. Positions where amino acids are substituted with alanine are shown.

DETAILED DESCRIPTION OF THE PREFERRED EMBODIMENTS

The present invention is based on the discovery by the present inventors of (a) at least one portion of CD14 that is necessary for binding of CD14 to LPS or gram-positive cell components and (b) additional regions on CD14 that are involved in inflammatory cellular responses mediated by CD14, such as production of IL-6 in response to gram negative or gram positive bacterial cell components (e.g., LPS from gram negative bacteria). The Examples below explain in detail the evidence supporting these discoveries.

Figure 1:
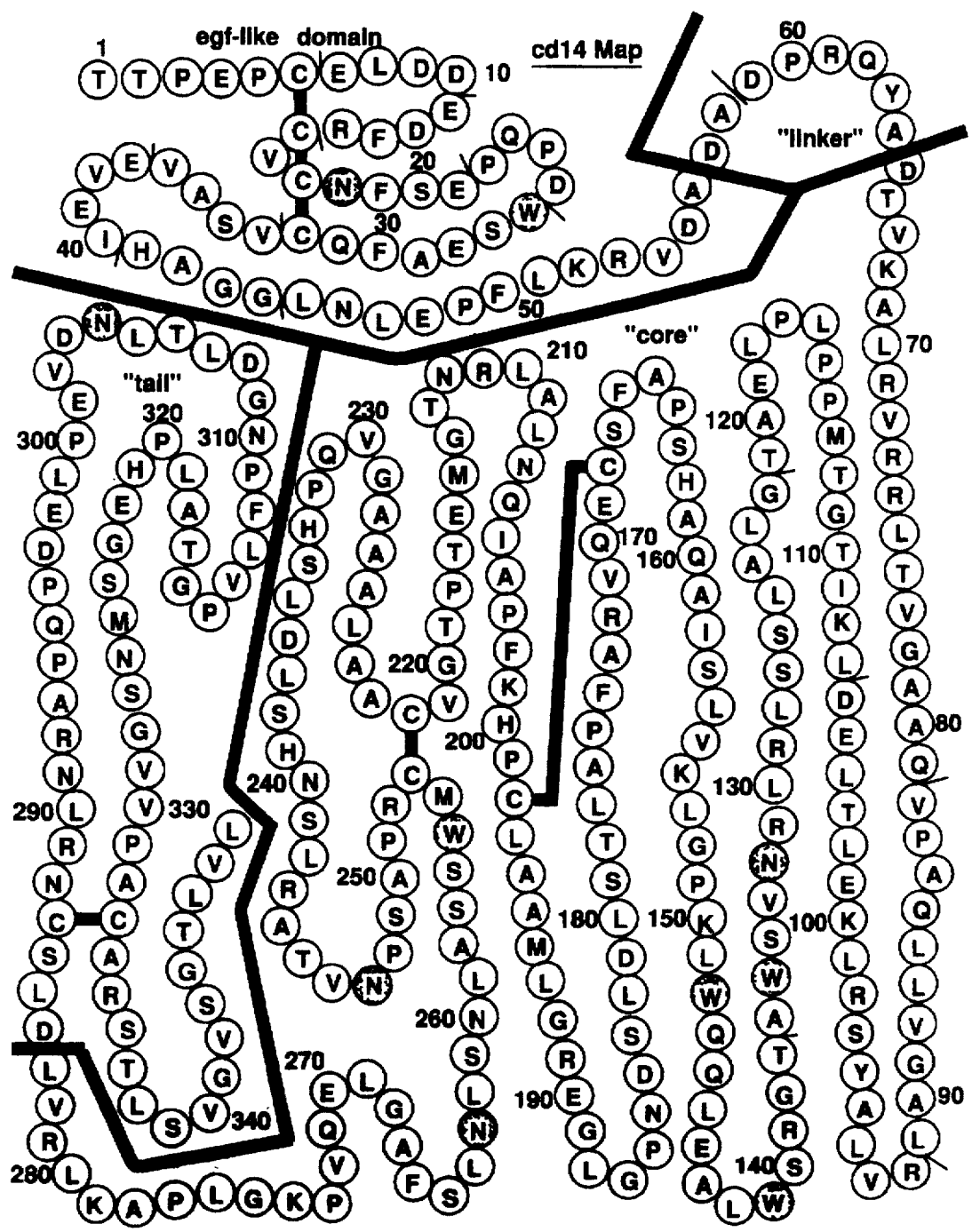
FIG. 1 shows a schematic map of human CD14 (SEQ ID NO:45).

FIG. 1 shows a map of human CD14, including the LPS binding region, corresponding to amino acids 57–64, and the IL-6 inducing regions, corresponding to amino acids 7 to 10 and 11 to 14.

The peptides of this invention may be linear or cyclic, of either or a mixture of D- or L-stereo chemistry (preferably all L-), chemically modified (as defined below), and in the form of physiologically acceptable salts (e.g., acetate or trifluoroacetate).

The linear peptides comprise the following amino acid sequence:

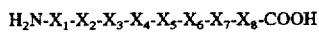

wherein,

X$_1$ is selected from the group consisting of Asp and Ser;
X$_2$ is selected from the group consisting of Ala, and Glu;
X$_3$ is selected from the group consisting of Asp and Glu;
X$_4$ is selected from the group consisting of Pro and Gly;
X$_5$ is selected from the group consisting of Arg and Lys;
X$_6$ is selected from the group consisting of Gln, Asn and His;
X$_7$ is selected from the group consisting of Tyr, Trp and Phe;
X$_8$ is selected from the group consisting of Ala and Ser;
and physiologically acceptable salts thereof; and further wherein said peptide binds to lipopolysaccharide.

As used herein "comprising" means that a peptide may include additional amino acids on either or both of the N- or C-termini of the given sequence. Preferably, these additional amino acids will correspond to the adjacent amino acids in CD14, as shown in such as FIG. 1. However, as long as the minimal structure such as X$_1$ to X$_8$, shown above, is present, the remaining chemical structure is relatively unimportant. Of course, any structure outside of the core, e.g., X$_1$ to X$_8$, structure should not significantly interfere with LPS or gram-positive cell component binding by the peptide. The peptides of this invention are generally from 8 to 60 amino acids in length, preferably 8 to 12 amino acids in length.

Some exemplary linear peptides of this invention are:

H$_2$N-Asp-Ala-Asp-Pro-Arg-Gln-Tyr-Ala-COOH (SEQ ID NO.7)

H$_2$N-Asp-Ala-Glu-Pro-Arg-Gln-Tyr-Ala-COOH (SEQ ID NO.8)

H$_2$N-Asp-Ala-Glu-Pro-Arg-Asn-Tyr-Ala-COOH (SEQ ID NO:9)

H$_2$N-Asp-Ala-Glu-Pro-Arg-Gln-Phe-Ala-COOH (SEQ ID NO:10)

H$_2$N-Asp-Ala-Glu-Pro-Arg-Asn-Phe-Ala-COOH (SEQ ID NO.11)

H$_2$N-Asp-Ala-Asp-Pro-Arg-Asn-Tyr-Ala-COOH (SEQ ID NO.12)

H$_2$N-Asp-Ala-Asp-Pro-Arg-Asn-Phe-Ala-COOH (SEQ ID NO.13)

H$_2$N-Asp-Ala-Asp-Pro-Arg-Gln-Phe-Ala-COOH (SEQ ID NO.14)

H$_2$N-Glu-Leu-Asp-Asp-Glu-Asp-Phe-Arg-COOH (SEQ ID NO.15)

Additional linear peptides useful for the purposes of this invention is the peptide corresponding to amino acids 7 to 64, inclusive, of the amino acid sequence of CD14, as shown in FIG. 1, and physiologically acceptable salts thereof.

The cyclic peptides of this invention comprise one of the following basic structures:

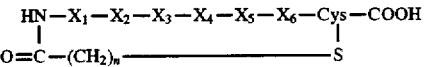

wherein,

X$_1$ is selected from the group consisting of Asp and Glu;
X$_2$ is selected from the group consisting of Pro and Gly;
X$_3$ is selected from the group consisting of Arg and Lys;
X$_4$ is selected from the group consisting of Gln, Asn and His;
X$_5$ is selected from the group consisting of Tyr, Trp and Phe;
X$_6$ is selected from the group consisting of Ala and Ser;
n is from 1 to 3; and physiologically acceptable salts thereof; and further wherein said peptide binds to lipopolysaccharide.

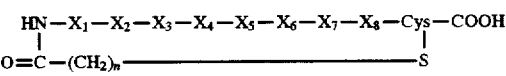

wherein,

X$_1$ is selected from the group consisting of Ala and Ser;
X$_2$ is selected from the group consisting of Asp and Glu;
X$_3$ is selected from the group consisting of Pro and Gly;
X$_4$ is selected from the group consisting of Arg and Lys;
X$_5$ is selected from the group consisting of Gln, Asn and His;
X$_6$ is selected from the group consisting of Tyr, Trp and Phe;
X$_7$ is selected from the group consisting of Ala and Ser;
X$_8$ is selected from the group consisting of Asp and Glu;
n is from 1 to 3; and physiologically acceptable salts thereof; and further wherein said peptide binds to lipopolysaccharide.

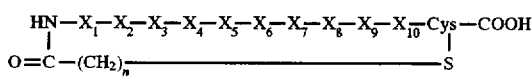

wherein, $X_1$ is selected from the group consisting of Asp and Glu;

$X_2$ is selected from the group consisting of Ala and Ser;

$X_3$ is selected from the group consisting of Asp and Glu;

$X_4$ is selected from the group consisting of Pro and Gly;

$X_5$ is selected from the group consisting of Arg and Lys;

$X_6$ is selected from the group consisting of Gln, Asn and His;

$X_7$ is selected from the group consisting of Tyr, Trp and Phe;

$X_8$ is selected from the group consisting of Ala and Ser;

$X_9$ is selected from the group consisting of Asp and Glu;

$X_{10}$ is selected from the group consisting of Thr and Ser;

n is from 1 to 3; and physiologically acceptable salts thereof; and further wherein said peptide binds to lipopolysaccharide.

Some exemplary cyclic peptides of this invention are:

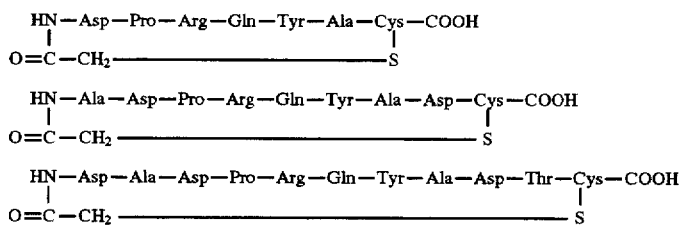

and, in each case, physiologically acceptable salts thereof.
For the above structures, it will be understood that

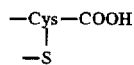

refers to the structure

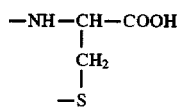

The second group of peptides comprises the following amino acid sequences:

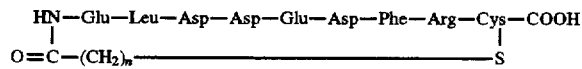

wherein n is from 1 to 3; or

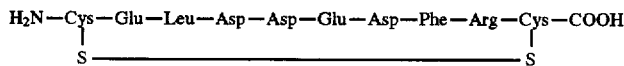

and, in each case, physiologically acceptable salts thereof. These peptides are expected to have the ability to inhibit inflammatory responses in cells, which may conveniently be measured by reduction of IL-6 production by such cells using, e.g., the method described in Example 10 below. Preferably the amount of IL-6 reduction will be at least 5-fold, particularly preferably, at least 10-fold (compared to when no peptide is present; see Example 10).

In each of the above cases, n is preferably 1. Also, in each case, the amino acids may be chemically derivatized as long as LPS binding or IL-6 inducing activity is not destroyed. Thus, "chemical derivatives" of the present peptides are included within the scope of the term "peptide" as used herein. These chemical derivatives contain additional chemical moieties not part of the unmodified peptide.

Covalent modifications of the peptide are included within the scope of this invention. Such modifications may be introduced into the molecule by reacting targeted amino acid residues of the peptide with an organic derivatizing agent that is capable of reacting with selected side chains or terminal residues.

Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK a of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4- ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptides or their functional derivatives to a water-insoluble support matrix or to other macromolecular carriers. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Other modifications include hydroxylation of proline and lysine, phosphorylation of hydroxyl groups of seryl or threonyl residues, oxidation of the sulfur atom in Cys, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups.

The activity of the peptide variant can be screened in a suitable screening assay for the desired characteristic. Biological activity is screened in an appropriate bioassay, as described herein. For example, binding of LPS to CD14 may be measured in a standard competitive binding assay. Activity to reduce cellular inflammatory responses may be measured in terms of reduction of IL-6 production by cells (e.g., U373 cells) as described herein.

Modifications of such peptide properties as redox or thermal stability, hydrophobicity, susceptibility to proteolytic degradation or the tendency to aggregate with carriers or into multimers are assayed by methods well known to the ordinarily skilled artisan.

Such derivatized moieties may improve the solubility, absorption, biological half life, and the like. The moieties may alternatively eliminate or attenuate any undesirable side effect of the protein and the like. Moieties capable of mediating such effects are disclosed, for example, in Remington's Pharmaceutical Sciences, 16th ed., Mack Publishing Co., Easton, Pa. (1980).

The peptides of the invention may also be covalently or noncovalently associated with a carrier molecule, such as a peptide or non-CD14 protein, a linear polymer (such as polyethylene glycol, polylysine, etc.), a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid; or a carbohydrate or oligosaccharide.

Figure 4A:
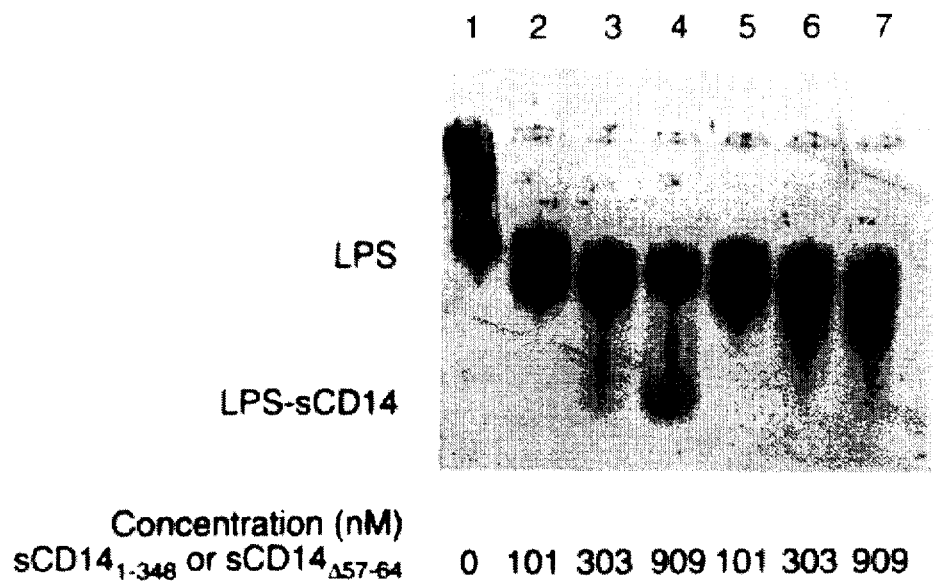
FIGS. 4A and 4B show that sCD14$_{\Delta 57\text{-}64}$ does not form stable complexes with $^3$H-LPS. Various concentrations of sCD14$_{1\text{-}348}$ (lanes 2–4) or sCD14$_{\Delta 57\text{-}64}$ (lanes 5–7) were incubated without rLBP (4A) or with 16.7 nM rLBP (4B) as described in Materials and Methods. Lane 1 contains LPS in the absence of additional protein. Mixtures were run on 4–20% native polyacrylamide gels and processed for fluorography. Positions of uncomplexed LPS and complexes between LPS and sCD14$_{1\text{-}348}$ are indicated.

The peptides of the first group (and also possibly the second group) of this invention are expected to have the ability to bind to LPS. This binding renders LPS unable to bind to CD14 and therefore produces an anti-inflammatory responses response in a mammal. They are also expected to bind to cellular components of gram positive cells that cause inflammatory (analogous to LPS; however, the structure(s) in gram positive bacteria that cause inflammatory responses to cells is (are) not yet known). "Binding" to LPS means that in a standard competition assay, the peptide is capable of inhibiting 50% binding of CD14 to LPS between 1 mM and 1 nM, preferably 100 μm to 10 nM ($IC_{50}$ values). A binding assay such as that in FIG. 4 may be carried out as is well known in the art.

The peptides of this invention may be made in a variety of ways. For example, solid phase synthesis techniques may be used. Suitable techniques are well known in the art, and include those described in Merrifield, in *Chem. Polypeptides*, pp. 335–61 (Katsoyannis and Panayotis eds. 1973); Merrifield, *J. Am. Chem. Soc.*, 85, 2149 (1963); Davis et al., *Biochem. Int'l*, 10, 394–414 (1985); Stewart and Young, *Solid Phase Peptide Synthesis* (1969); U.S. Pat. No. 3,941,763; Finn et al., in *The Proteins*, 3rd ed., vol. 2, pp. 105–253 (1976); and Erickson et al. in *The Proteins*, 3rd ed., vol. 2, pp. 257–527 (1976). Solid phase synthesis is the preferred technique of making individual peptides since it is the most cost-effective method of making small peptides.

The peptide may also be made in transformed host cells using recombinant DNA techniques. To do so, a recombinant DNA molecule coding for the peptide is prepared. Methods of preparing such DNA molecules are well known in the art. For instance, sequences coding for the peptides could be excised from DNA using suitable restriction enzymes. Alternatively, the DNA molecule could be synthesized using chemical synthesis techniques, such as the phosphoramidite method. Also, a combination of these techniques could be used.

The invention also includes a vector capable of expressing the peptides in an appropriate host. The vector comprises the DNA molecule that codes for the peptides operatively linked to appropriate expression control sequences. Methods of effecting this operative linking, either before or after the DNA molecule is inserted into the vector, are well known. Expression control sequences include promoters, activators, enhancers, operators, ribosomal binding sites, start signals, stop signals, cap signals, polyadenylation signals, and other signals involved with the control of transcription or translation.

The resulting vector having the DNA molecule thereon is used to transform an appropriate host. This transformation may be performed using methods well known in the art.

Any of a large number of available and well-known host cells may be used in the practice of this invention. The selection of a particular host is dependent upon a number of factors recognized by the art. These include, for example, compatibility with the chosen expression vector, toxicity to it of the peptides encoded for by the DNA molecule, rate of transformation, ease of recovery of the peptides, expression characteristics, bio-safety and costs. A balance of these factors must be struck with the understanding that not all hosts may be equally effective for the expression of a particular DNA sequence.

Within these general guidelines, useful microbial hosts include bacteria (such as *E. coli* sp.), yeast (such as Saccharomyces sp.) and other fungi, insects, plants, mammalian (including human) cells in culture, or other hosts known in the art.

Next, the transformed host is cultured under conventional fermentation conditions so that the desired peptides are expressed. Such fermentation conditions are well known in the art.

Finally, the peptides are purified from the culture. These purification methods are also well known in the art.

To synthesize the cyclic peptides, the procedure set forth in Example 8 may be used.

The peptides of this invention may be used in any of a number of situations where LPS/gram positive cell component binding is required. For example, therapeutically and prophylactically, the peptides may be used for inflammatory bowel disease, acute and chronic liver failure, graft vs. host disease (bone marrow transplant), intestinal or liver transplant, ARDS, acute pancreatitis and tuberculosis. Septic shock is a particularly preferred target condition.

The novel peptides are useful for the prophylaxis or treatment of septic shock in mammals, including humans, at doses of about 0.1 to 100 mg/kg of body weight, preferably at a level of about 1 to 50 mg/kg of body weight, and the amount may be administered, e.g., in divided doses on daily basis. The peptides may be administered prophylactically to patients who may be exposed to or have been exposed to organisms which may cause septic shock or to detoxify LPS (bacterial endotoxins) by the use of the same dose set forth above in vivo. In vitro detoxification or prevention of endotoxin contamination may be carried out at a level which is effective to achieve the desired result. The amount may be based on routine experimentation based on the premise that about 1 mole of endotoxin is bound by 1 mole of peptide. The particular dose of a particular peptide may be varied within or without the range that is specified herein depending on the particular application or severity of a disease and the condition of the host. Those who are skilled in the art may ascertain the proper dose using standard procedures.

The protein or pharmaceutical compositions of the present invention may be administered by any means that achieve their intended purpose. For example, administration may be by parenteral routes, including subcutaneous, intravenous, intradermal, intramuscular, intraperitoneal, intrathecal, transdermal, or buccal routes. Alternatively, or concurrently, administration may be by the oral or rectal route. The proteins and pharmaceutical compositions can be administered parenterally by bolus injection or by gradual perfusion over time.

In addition to the peptide, these pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to about 99 percent, preferably from about 25–85 percent, of active compound(s), together with the excipient.

Suitable excipients are, in particular, fillers such as sugars, such as lactose, sucrose, mannitol, or sorbitol; cellulose preparations and/or calcium phosphates, such as tricalcium phosphate or calcium hydrogen phosphate; as well as binders such as starch paste made using, for example, maize starch, wheat starch, rice starch, potato starch, gelatin, gum tragacanth, methyl cellulose, hydroxypropylmethylcellulose, sodium carboxymethyl cellulose, and/or polyvinylpyrrolidone. If desired, disintegrating agents may also be added, such as the above-mentioned starches as well as carboxymethyl starch, cross-linked polyvinyl pyrrolidone, agar, or alginic acid or a salt thereof, such as sodium alginate. Auxiliaries which can be used in the compositions according to the present invention include flow-regulating agents and lubricants such as silica, talc, stearic acid or salts thereof, and/or polyethylene glycol.

The peptides of this invention are also useful to detect the presence of inflammatory gram positive or gram negative bacterial cell components, such as LPS from gram negative bacteria, in a sample such as a body fluid (i.e., blood, urine, CSF, saliva, etc.) or any other sample that might contain LPS or a gram positive cell component. Standard methodology can be used to carry out such a test.

Also included within the scope of the present invention is an antibody specific for the peptides disclosed herein, or specific for a functional derivative thereof.

The term "antibody" refers both to monoclonal antibodies which are a substantially homogeneous population and to polyclonal antibodies which are heterogeneous populations. Polyclonal antibodies are derived from the sera of animals immunized with an antigen. Monoclonal antibodies (mAbs) to specific antigens may be obtained by methods known to those skilled in the art. See, for example Kohler and Milstein, *Nature* 256:495–497 (1975) and U.S. Pat. No. 4,376,110. Such antibodies may be of any immunoglobulin class including IgG, IgM, IgE, IgA, IgD and any subclass thereof.

The term "antibody" is also meant to include both intact molecules as well as fragments thereof, such as, for example, Fab and F(ab')2, which are capable of binding antigen. Fab and F(ab')2 fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')2 and other fragments of the antibodies useful in the present invention may be used for the detection and quantitation of the protein of the present invention in the same manner as an intact antibody. Such fragments are typically produced by proteolytic cleavage, using enzymes such as papain (to produce Fab fragments) or pepsin (to produce F(ab')2 fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopic determinants usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

One group of antibodies of this invention are those that bind specifically to the epitopes consisting at most of amino acids 7–14 or 57–64 of CD14. Although the existence and importance of these epitopic regions has not been appreciated prior to this invention, the inventors recognize that the MEM18 antibody (see Examples section) has as its epitope, amino acids 57–64, and antibody 3C10 has as its epitope(s) amino acids 7–10 and 11–14 of CD14. Thus, these antibodies are excluded from the claims herein.

Nevertheless, until the present invention, it was not appreciated whether and how to make any additional antibodies against these epitopes. For example, prior to this invention, anti-CD14 antibodies were generally made by employing full-length or soluble CD14 as the antigen. The present invention makes it possible to generate additional antibodies against these important epitopes by using the peptides of this invention as antigens, thus insuring that substantially all of the generated antibodies will be against the desired epitope (s).

The antibodies may be useful therapeutically in the same manner as the peptides described herein, and, accordingly, that disclosure is to be read as including the antibodies also.

The antibodies, or fragments of antibodies, of the present invention may be further used to quantitatively or qualitatively detect the presence of the peptides disclosed herein, or of intact CD14 containing the epitope recognized by the antibody. For example, it would be of benefit to monitor the level of a peptide in the circulation or in the tissues of a subject receiving therapeutic doses of the peptide.

An assay for the peptides disclosed herein typically comprises incubating a biological sample from the subject in the presence of a detectably labeled antibody or antibody fragment capable of identifying the protein and detecting the antibody which is bound in the sample.

Thus, in this aspect of the invention, a biological sample may be treated with nitrocellulose, or other solid support which is capable of immobilizing cells, cell particles or soluble proteins. The support may then be washed with suitable buffers followed by treatment with the detectably labeled specific antibody. The solid phase support may then be washed with the buffer a second time to remove unbound antibody. The amount of bound label on said solid support may then be detected by conventional means.

By "solid phase support" or "carrier" is intended any support capable of binding antigen (i.e., the peptide) or antibodies. Well-known supports, or carriers, include glass, polystyrene, polypropylene, polyethylene, dextran, nylon, amylases, natural and modified celluloses, polyacrylamides, agaroses, and magnetite. The nature of the carrier can be either soluble to some extent or insoluble for the purposes of the present invention. The support material may have virtually any possible structural configuration so long as the coupled molecule is capable of binding to the antibody. These support materials may also be used to immobilize the peptides for uses such as detection or removal of LPS from samples.

The binding activity of an antibody specific for the peptides disclosed herein may be determined according to well known methods, such as enzyme immunoassay (EIA) or radioimmunoassay (RIA). Those skilled in the art will be able to determine operative and optimal assay conditions for each determination by employing routine experimentation.

For EIA, the antibody is detectably labeled by linking to an enzyme. This enzyme, in turn, when later exposed to its substrate, will react with the substrate in such a manner as to produce a chemical moiety which can be detected, for example, by spectrophotometric, fluorometric or by visual means. Enzymes which can be used to detectably label the antibody include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the antibody or peptide, it is possible to detect binding through the use of a RIA. See, for example: Weintraub, B., *Principles of Radioimmunoassays*, Seventh Training Course on Radioligand Assay Techniques, The Endocrine Society, March, 1986, pp. 1–5, 46–49 and 68–78; Work, T. S. et al., *Laboratory Techniques and Biochemistry in Molecular Biology*, North Holland Publishing Company, NY, 1978. The radioactive isotope can be detected by such means as the use of a gamma counter or a scintillation counter or by autoradiography.

It is also possible to label the antibody or peptide with a fluorescent compound. When the fluorescently labeled species is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody or peptide can also be detectably labeled using fluorescence emitting metals such as <152> Eu, or others of the lanthanide series. These metals can be attached to the antibody or peptide using such metal chelating groups as diethylenetriaminepentaacetic acid (DTPA) or ethylenediaminetetraacetic acid (EDTA).

The antibody or peptide can also be detectably labeled by coupling it to a chemiluminescent compound. The presence of the chemiluminescent-tagged species is then determined by detecting the presence of luminescence that arises during the course of a chemical reaction. Examples of particularly useful chemiluminescent labeling compounds are luminol, isoluminol, the aromatic acridinium ester, imidazole, acridinium salt and oxalate ester.

Likewise, a bioluminescent compound may be used to label the antibody or peptide of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

It is understood that the application of the teachings of the present invention to a specific problem or situation will be within the capabilities of one having ordinary skill in the art in light of the teachings contained herein. Examples of the products of the present invention and representative processes for their isolation, use, and manufacture appear below.

EXAMPLES

Materials and Methods

Reagents

Recombinant soluble CD14 (rsCD14) and recombinant LBP (rLBP) were constructed and purified as described (Hailman, E., et al. *J. Exp. Med.* 179, 269–277 (1994). Concentrations of all purified proteins were determined with a Micro BCA protein kit (Pierce, Rockford, Ill.) according to manufacturer's specification. Since full-length rsCD14 terminates at position 348 of the mature protein (Hailman et al., *Ibid.* (1994)), we herein refer to it as $sCD14_{1-348}$. The anti-CD14 mAbs used were 3C10 [purified by chromatography on Protein G from the conditioned medium (CM) of ATCC TIB 228], MEM-18 (SANBIO, The Netherlands), My4 (Coulter Immunology, Hialeah, Fla.), and 60b (Todd, R. F., et al., *Hybridoma* 1, 329–337 (1982). Rabbit polyclonal anti-human CD14 antiserum was raised against $sCD14_{1-348}$ and was prepared by Antibodies, Inc. (Davis, Calif.). Enzymes for DNA manipulation and polymerase chain reaction (PCR) were purchased from Boehringer Mannheim (Indianapolis, Ind.), p-nitro blue tetrazolium chloride (NBT), 5-bromo-4-chloro-3-indolyl phosphate salt (BCIP), and alkaline phosphatase-conjugated goat anti-rabbit IgG were purchased from BioRad (Richmond, Calif.).

Site-directed Mutagenesis

A cDNA which encodes mutant sCD14 lacking amino acids 57–64 (sCD14$_{\Delta 57-64}$) was constructed using a Transformer site-directed mutagenesis kit (Clontech, Palo Alto, Calif.) according to the protocol specified by the manufacturer. Briefly, mutation primer (5'-TAAAGCGCGTCGATGCGGACACGGTCAAGGCTC-TCC-3') (SEQ ID NO.16) and selection primer (Trans oligo Ssp 1/EcoR V, Clontech) were annealed to a mammalian expression vector (pDSRα2) containing the cDNA for sCD14$_{1-348}$ (Hailman et al., Ibid. (1994)). Primers were extended and ligated using T4 DNA polymerase/T4 DNA ligase for 2 h. The reaction was digested with Ssp I to linearize un-mutated wild-type plasmids and undigested circular plasmids which contained mutagenized DNA were transformed into E. coli strain DH5α. Plasmid DNA was isolated from transformants and DNA sequence analysis verified the presence of the deletion.

The Transformer site-directed mutagenesis kit was also used to generate mutant cDNAs encoding sCD14 having alanine substituted at various position between amino acids 59 and 65. For these experiments, the following mutant primers were used:

5'-GATGCGGACGCCGCCCCTAGGCAGTATGCTGAC-ACG-3' (SEQ ID NO.17) for sCD14$_{D59A}$,

5'-GATGCGGACGCCGACGCGCGGCAGTATGCTGAC-3' (SEQ ID NO.18) for sCD14$_{P60A}$,

5'-GCGGACGCCGACCCTGCGCAGTATGCTGACAC-3' (SEQ ID NO.19) for sCD14$_{R61A}$,

5'-GACGCCGACCCGCGAGCGTATGCTGACACGGTC-3' (SEQ ID NO.20) for sCD14$_{Q62A}$,

5'-CGCCGACCCGCGTCAGGCTGCTGACACGGTTCAAG-3' (SEQ ID NO.21) for sCD14$_{Y63A}$,

5'-CCGCGGCAGTATGCTGCCACGGTCAAGGCTCTCC-3' (SEQ ID NO.22) for sCD14$_{D65A}$, and

5'-GTCGATGCGGACGCCGCCGCGGCGGCGGCTG-CTGCCACGGTCAAGGCTCTCCGC-3' (SEQ ID NO.23) for sCD14$_{(59-65)A}$. Introduction of the appropriate mutation in all cDNAs was confirmed by DNA sequencing.

Transient Expression of Mutant sCD14 Proteins in COS-7 Cells

To express mutant sCD14 proteins, mammalian expression vectors containing mutant sCD14, cDNAs were introduced into COS-7 (ATCC CRL 1651) cells by electroporation. Expression of mutant sCD14 was analyzed by Western blot and the concentration of mutant proteins was determined with the aid of a BIAcore biosensor instrument (Pharmacia Biosensor, Piscataway, N.J.) using protocols described by the manufacturer.

Purification of sCD14$_{\Delta 57-64}$

The expression vector containing the cDNA encoding sCD14$_{\Delta 57-64}$ was stably transfected into Chinese hamster ovary (CHO) cells deficient in dihydrofolate reductase as described (Hailman, E., et al., J. Exp. Med. 179, 269–277 (1994)). A single clone was grown without serum to generate CM containing sCD14$_{\Delta 57-64}$. Mutant protein was purified by immunoaffinity chromatography on a column to which mAb 3C10 was coupled to Sepharose 4B (Pharmacia, Piscataway, N.J.). Briefly, CM was concentrated 20× using a S10Y10 spiral-wound cartridge (Amicon, Beverly, Mass.). Concentrated CM was passed over the column pre-equilibrated with phosphate-buffered saline (PBS, GIBCO-BRL) and protein was monitored by following the absorbance at 280 nm. The column was washed with PBS until the absorbance reached baseline. The protein was then eluted with 0.1M glycine-HCl, pH 2.5 into collection tubes containing 0.5M phosphate, pH 8.0. sCD14$_{\Delta 57-64}$-containing fractions were pooled, concentrated, and diafiltered into PBS in a Centriprep-10 (Amicon, Beverly, Mass.) concentrator. Purity of the sample was checked by SDS-polyacrylamide gel electrophoresis (SDS-PAGE) followed by silver staining or Coomassie Blue staining.

Native PAGE Assay

Variations of a previously described native PAGE assay (Hailman, et al., Ibid. (1994) and the description of FIG. 2) were used to assess whether unpurified or purified sCD14 preparations bound LPS. For unpurified sCD14 expressed in CM of COS-7 cells, 30 µl of CM was incubated at 37° C. with various amounts of LPS (Salmonella minnesota type Re595, List Biological Laboratories, Campbell, Calif.) for 30 min and mixtures were resolved by native PAGE on 10% gels (Noval Experimental Technologies). Proteins were then transferred to nitrocellulose membranes and Western blot analysis was performed as previously described (Hailman et al., Ibid. (1994)) using anti-human CD14 polyclonal antibody.

To assess LPS-binding of purified sCD14 preparations, sCD14$_{1-348}$ or sCD14$_{\Delta 57-64}$ were incubated at various concentrations (0, 101, 303, and 909 nM) with 3 µg/ml of $^3$H-LPS prepared from E. coli K12 strain LCD25 (List Biological Laboratories, Menlo Park, Calif.) in the presence or absence of 16.7 nM rLBP. The reaction was incubated at 37° C. for 30 min and then electrophoresed on native 4–20% polyacrylamide gels. Gels were prepared for fluorography as previously described (Hailman, et al., Ibid. (1994)).

Experiments were also performed to determine whether various CD14 mAbs could compete with LPS for binding to sCD14. In these studies, $^3$H-LPS-sCD14 complexes were formed by incubating 130 µg/ml sCD14$_{1-348}$ with 10 µg/ml $^3$H-LPS for 15 h at 37° C. in PBS with 1 mM EDTA. Complexes were then diluted 10-fold and incubated 20 min at 37° C. with 200 µg/ml various mAbs in a total volume of 10 µl. Mixtures were then electrophoresed on 8–16% native gels and processed for fluorography as above.

In other experiments, we examined whether rLBP could lower the effective dose of LPS required to competitively inhibit binding of MEM-18 or 3C10 to sCD14. MEM-18 or 3C10 (40 µg/ml) was incubated with sCD14$_{1-348}$ (2.6 µg/ml) for 10 min at 37° C. Various concentrations of LPS (from S. minnesota strain R60, List Biological Laboratories) were then added in the presence or absence of rLBP (1 µg/ml) for 20 min at 37° C. in a total volume of 10 µl. Mixtures were then electrophoresed on 8–16% native gels and transferred to nitrocellulose in Tris-glycine buffer with 20% methanol. The nitrocellulose was blocked in PBS with 10% dry milk, and incubated with polyclonal antibodies in PBS with 0.1% dry milk. CD14 was detected using a rabbit polyclonal antibody (generous gift of Dr. Pat Detmers) raised against sCD14$_{1-348}$ and an alkaline phosphatase-conjugated secondary antibody. Bound antibody was detected using NBT and BCIP according to the manufacturer's instruction.

Activation of Polymorphonuclear Leukocytes (PMN) by LPS and sCD14

The ability of rLBP and sCD14$_{\Delta 57-64}$ or sCD14$_{1-348}$ to enable PMN adhesion to fibrinogen-coated plates was assessed by previously established protocols (Hailman, et al., Ibid. (1994) and Detmers et al., J. Immunol. 152:2137–2145 (1994)). Briefly, PMN were incubated for 10 min with LPS, LBP, and sCD14$_{1-348}$, washed and adhesion to fibrinogen-coated surfaces was measured.

U373 Bioassays

Growth of U373 cells, activation by COS-7 CM containing sCD14 or by purified sCD14 preparations, and quantitation of IL-6 were performed exactly as described (Frey, et al., *J. Exp. Med.* 176:1665–1671 (1992)). Briefly, mixtures of sCD14$_{1-348}$ and LPS were added to monolayers of U373 cells in serum-free medium and incubated for 24 h. IL-6 in the supernatant was then measured by ELISA.

BIAcore Analyses of Interactions Between sCD14 and anti-CD14 mAbs

Recognition of sCD14 preparations by anti-CD14 mAbs was performed with a BIAcore biosensor instrument. The instrument, CM5 sensor chips, and amine coupling kit were purchased from Pharmacia Biosensor (Piscataway, N.J.). Briefly, mAb 3C10 (200 μg/ml in 20 mM sodium acetate, pH 3.4) was immobilized to a CM5 sensor chip by amine coupling according to manufacturer's specifications. The flow cell immobilized with 3C10 was then incubated in succession with 4 solutions as detailed in the following steps: Step 1, COS-7 CM or 10 μg/ml purified sCD14$_{\Delta57-64}$ for 2 min; Step 2, HBS buffer [10 mM N-2-hydroxyethylpiperazine-N'-2-ethanesulfonic acid, pH 7.5, 0.15M NaCl, 3.4 mM EDTA, 0.005% (V/V) surfactant P20 (Pharmacia Biosensor)] for 2 min; Step 3, 50 μg/ml MEM-18 (in HBS buffer) for 2–3 min; Step 4, HBS buffer for 2 min. All solutions were injected at a flow rate of 5 μl/min. To quantitate the binding of MEM-18 to sCD14 mutants in COS-7 CM, we calculated a relative response unit (RRU). RRU was obtained by subtracting the response unit (RU) recorded just before injection of MEM-18 from the RU recorded after injection of MEM-18 and a 2 min wash. Since there are slight differences in the concentrations of sCD14 proteins expressed in CM, and since the signal is linearly related to the concentration of sCD14 under the condition employed, we present binding data as RRU per nM sCD14 mutants.

Example 1

LPS Does Not Bind to sCD14$_{\Delta57-64}$ Expressed in COS-7 CM

We have found that endoproteinase AspN cleaves sCD14 before aspartic acid residues 57, 59, 64 and that these cleavage sites are masked when LPS is complexed to sCD14 (data not shown). This observation suggested that the region between amino acids 57 and 65 could be important for LPS binding. To test this hypothesis, we utilized the technique of site-directed mutagenesis to construct a cDNA which encodes mutant sCD14 (sCD14$_{\Delta57-64}$) lacking amino acids 57–64. A mammalian expression vector containing sCD14$_{\Delta57-64}$ was transiently transfected into COS-7 cells and serum-free CM was collected. Western blot analysis (data not shown) revealed that expression of sCD14$_{\Delta57-64}$ was comparable to expression of sCD14$_{1-348}$ in COS-7 transfected cells.

Figure 2:
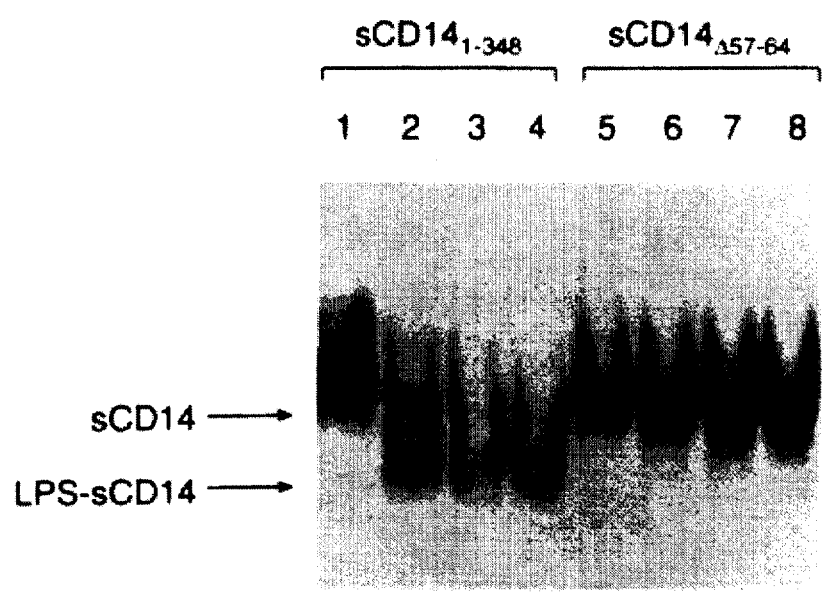
FIG. 2 shows that COS-7 CM containing sCD14$_{\Delta 57\text{-}64}$ does not form complexes with LPS. Thirty μL of CM containing sCD14$_{1\text{-}348}$ or sCD14$_{\Delta 57\text{-}64}$ were incubated with 1 μg (lanes 2 and 6), 2 μg (lanes 3 and 7), or 5 μg (lanes 4 and 8) of Re 595 LPS for 30 min at 37° C. Lanes 1 and 5 represent CM alone without LPS. Protein mixtures were run on 10% native polyacrylamide gels and then transferred to nitrocellulose membranes. sCD14$_{1\text{-}348}$ was detected using polyclonal anti-human CD14 antiserum. The position of sCD14$_{1\text{-}348}$ alone or LPS-sCD14$_{1\text{-}348}$ complexes are indicated by arrows.

We then used a native PAGE assay to assess whether sCD14$_{\Delta57-64}$ present in COS-7 CM binds LPS. CM containing sCD14$_{1-348}$ or sCD14$_{\Delta57-64}$ were incubated with increasing amounts of LPS and the mixtures were electrophoretically transferred to nitrocellulose membranes. sCD14 or sCD14-LPS complexes were then detected with anti-CD14 polyclonal antiserum. FIG. 2 shows that LPS caused a shift in the electrophoretic mobility of sCD14$_{1-348}$, and this shift is caused by binding of LPS to CD14 (Hailman, et al., *Ibid.* (1994)). In contrast, no shift was observed in CM containing sCD14$_{\Delta57-64}$ even at an LPS concentration 5-fold higher then that needed to completely shift sCD14$_{1-348}$. These results are consistent with the notion that amino acids 57–64 in sCD14 are necessary for LPS binding.

Example 2

Purification and Characterization of sCD14$_{\Delta57-64}$

Figure 3:
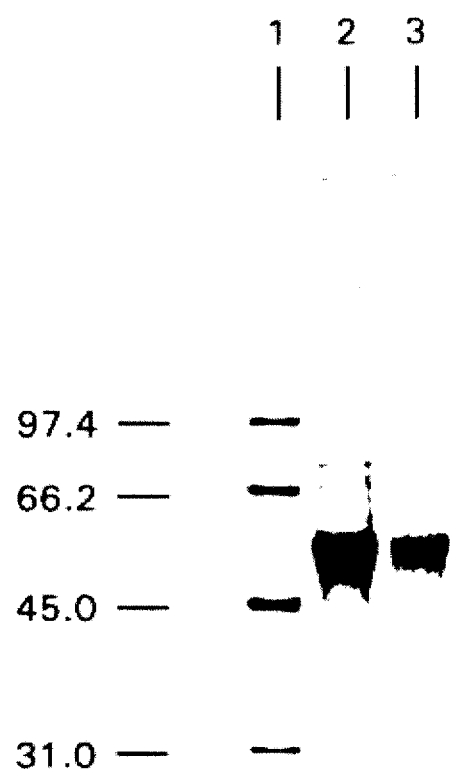
FIG. 3 shows purification of sCD14$_{\Delta 57\text{-}64}$. sCD14$_{\Delta 57\text{-}64}$ was analyzed by SDS-PAGE on 4–20% gels followed by Coomassie Brilliant Blue staining. All samples were heated at 90° C. for 3 min in sample buffer [62.5 mM Tris-HCl, pH 6.8, 2% SDS, 0.005% Bromphenol blue, 10% glycerol, 10% (v/v) b-mercaptoethanol] prior to loading. Lane 1, 10 μg of Mark-12 molecular weight markers (Noval Experimental Technologies); lane 2, 5 μl of CM; lane 3, 20 μl of pooled fraction containing sCD14$_{\Delta 57\text{-}64}$ eluted from 3C10 affinity column.

To further characterize the LPS-binding and biological activities of sCD14$_{\Delta57-64}$, it was necessary to purify large quantities of the mutant protein. Therefore, a stable CHO cell line expressing sCD14$_{\Delta57-64}$ was constructed and mutant protein was purified from the serum-free CM of this cell line. FIG. 3 shows that purified sCD14$_{\Delta57-64}$ migrated with an apparent Mr of 55,000 when analyzed by reducing SDS-PAGE. In order to determine whether the deletion in sCD14$_{\Delta57-64}$ affected protein structure, we analyzed purified sCD14$_{\Delta57-64}$ and sCD14$_{1-348}$ by CD. Both the far and near UV spectra of the sCD14$_{\Delta57-64}$ were within experimental error of sCD14$_{1-348}$, as was the thermal stability determined by change in CD signal with temperature (data not shown). This result suggests that the deletion does not significantly interfere with the folding structure or stability of sCD14. Furthermore, the data also imply that Tyr at position 63 does not contribute to the spectrum of the native protein and that this residue therefore is located in a flexible or symmetrical environment. This is consistent with the theory that the region between amino acids 57–64 is a flexible bridge connecting two compactly folded domains.

Example 3

Purified sCD14$_{\Delta57-64}$ Does Not Form a Stable Complex with LPS

Figure 4B:
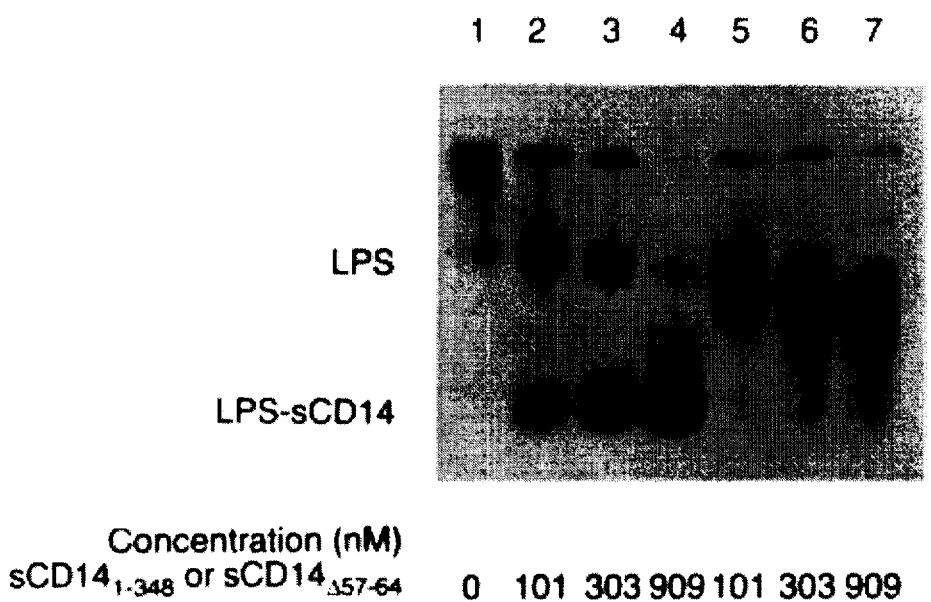

To directly address whether sCD14$_{\Delta57-64}$ is capable of binding LPS, we used the native PAGE assay to detect stable complexes between sCD14$_{1-348}$ or sCD14$_{\Delta57-64}$ and $^3$H-LPS. Incubation of sCD14$_{1-348}$ with LPS for 30 min lead to stable complexes (FIG. 4A), and addition of rLBP dramatically accelerated this process (FIG. 4B). In contrast, even the highest concentration of sCD14$_{\Delta57-64}$ did not support complex formation with $^3$H-LPS in the absence (FIG. 4A, lanes 5–7) or presence (FIG. 4B, lanes 5–7) of rLBP. These data confirm that sCD14$_{\Delta57-64}$ fails to bind LPS.

Example 4 sCD14$_{\Delta57-64}$ Does not Enable Cellular Responses to LPS

Figure 5:
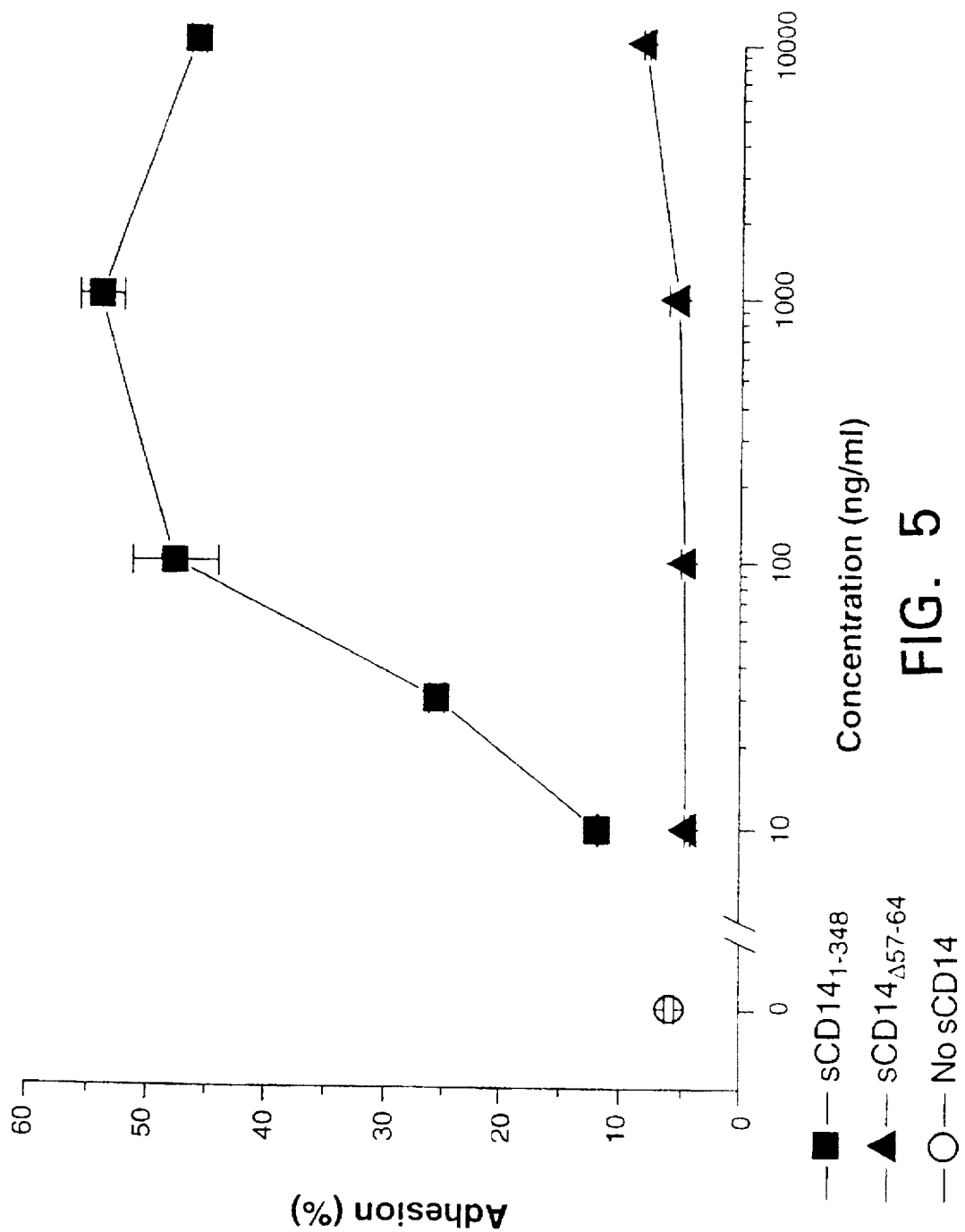
FIG. 5 shows sCD14$_{1\text{-}348}$ but not sCD14$_{\Delta 57\text{-}64}$ mediates responses of PMN to LPS and LBP. Freshly isolated PMN were incubated with "smooth" LPS (*E. coli* 0111:B4, 30 ng/ml), rLBP (1 μg/ml), and the indicated concentrations of sCD14$_{1\text{-}348}$ or sCD14$_{\Delta 57\text{-}64}$ for 10 min at 37° C. Cells were washed and adhesion to fibrinogen-coated wells was measured (Hailman, et al., *J. Exp. Med.* 179: 269–277 (1994) and Van Kessel, K. P. M. et al., *J. Immunol. Methods* 172: 25–31 (1994)). Error bars indicate standard deviations of triplicate determinations.

The lack of interaction between sCD14$_{\Delta57-64}$ and LPS suggested that the mutant protein would be impaired in its ability to enable cellular responses to LPS. We tested this hypothesis by using two previously characterized assays (Hailman, E., et al., *J. Exp. Med.* 179, 269–277 (1994); Juan, T. S., et al., *J. Biol. Chem.* in press; Frey, E. A., et al., *J. Exp. Med.* 176, 1665–1671 (1992)) which measure sCD14 function. In the first assay, we examined whether sCD14$_{\Delta57-64}$ could enable LPS-induced adhesion of PMN to fibrinogen. FIG. 5 shows that 100 ng/ml sCD14$_{1-348}$ enabled a strong adhesive response of PMN to smooth LPS and rLBP. However, no response was seen even when 10,000 ng/ml sCD14$_{\Delta57-64}$ was added.

Figure 6:
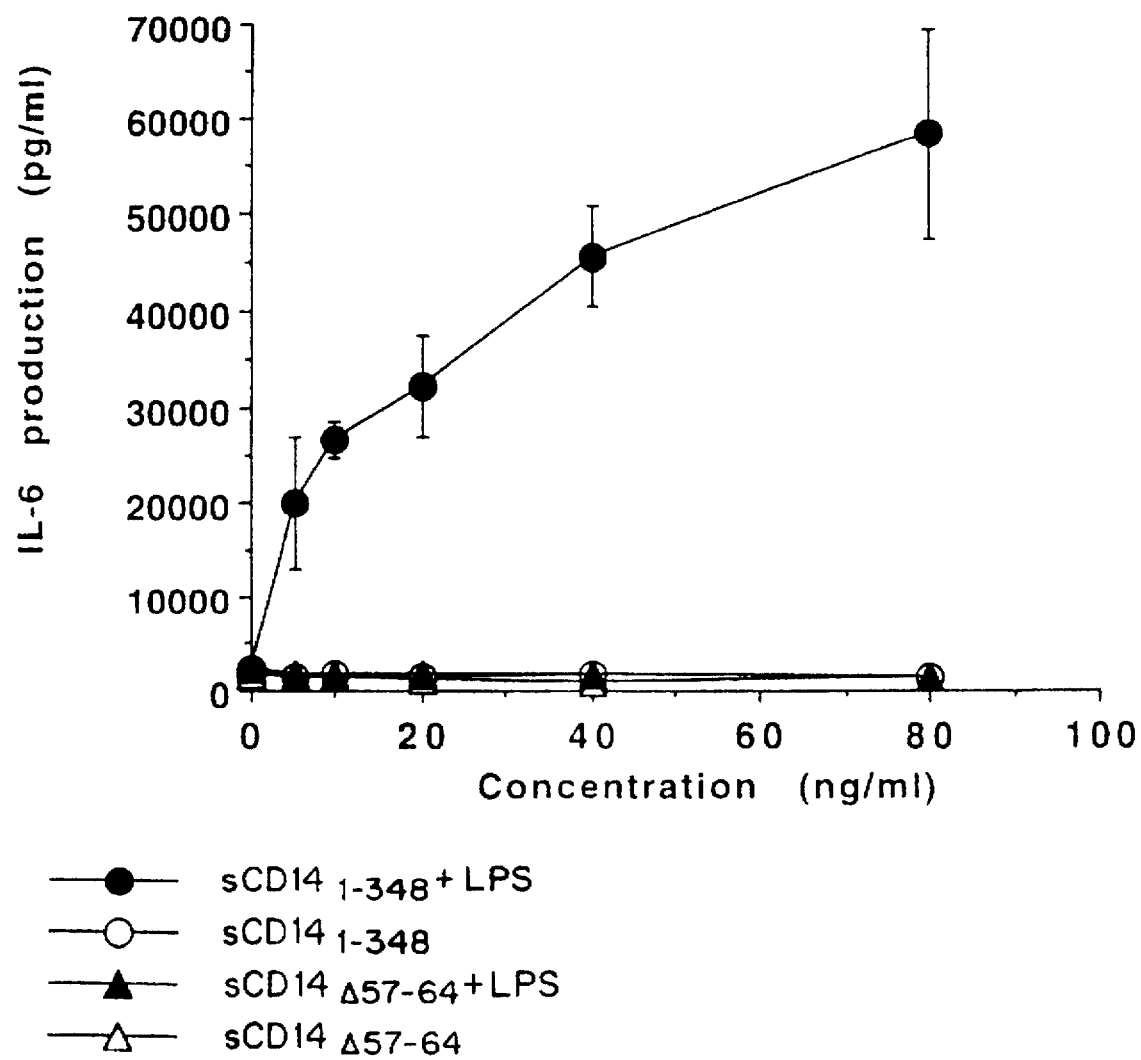
FIG. 6 shows that sCD14$_{\Delta 57\text{-}64}$ does not induce IL-6 production in U373 cells. U373 cells were treated with various concentrations of sCD14$_{1\text{-}348}$ or sCD14$_{\Delta 57\text{-}64}$ in the presence or absence of LPS (10 ng/ml) for 24 h. IL-6 levels were determined by an IL-6 ELISA. Data presented are means ± standard deviations from four readings.

We also examined the ability of sCD14$_{\Delta57-64}$ to support responses of U373 cells to LPS. Addition of as little as 5 ng/ml sCD14$_{1-348}$ enabled strong IL-6 production in response to LPS (FIG. 6), confirming previous reports (Frey, E. A., et al., *J. Exp. Med.* 176, 1665–1671 (1992)). In contrast, sCD14$_{\Delta 57-64}$ failed to support LPS-dependent IL-6 production even at a concentration of 80 ng/ml. These findings confirm that residues 57–64 are crucial to the biological function of sCD14$_{1-348}$.

Example 5

An Epitope for mAb MEM-18 is Localized to Amino Acids 57–64

Figure 7A:
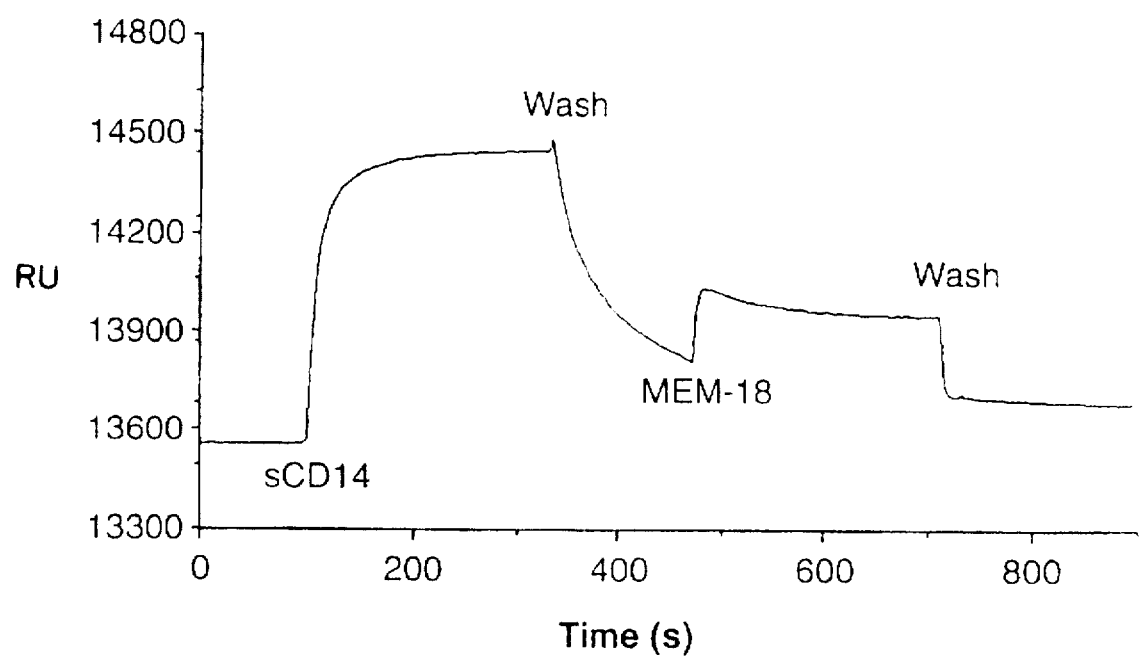
FIGS. 7A and 7B show that mAb MEM-18 does not recognize sCD14$_{\Delta 57\text{-}64}$. 7A. Immobilization of mAb 3C10 to a sensor chip and injection of solutions at various "Steps" are detailed in the Examples section below. "Wash" indicates a washing step using HBS buffer. Binding of purified proteins to mAbs was assessed by measuring change in Response Unit (RU) after a 2 min wash. 7B. Various amounts (2 ng for lanes 1, 2, 3 and 5; 10 ng for lanes 4 and 6) of purified sCD14$_{1\text{-}348}$ (lanes 1, 3, and 4) or sCD14$_{\Delta 57\text{-}64}$ (lanes 2, 5, and 6) were electrophoresed on 4–20% SDS-PAGE and proteins were transferred to nitrocellulose membranes. For detection of sCD14 protein, polyclonal anti-CD14 antiserum (lanes 1 and 2) or mAb MEM-18 (lanes 3–6) were incubated with the filters for 1 h. Immune complexes were detected by enhanced chemiluminescence (ECL, Amersham, Arlington Heights, Ill.) as described by the manufacturer.
Figure 7B:
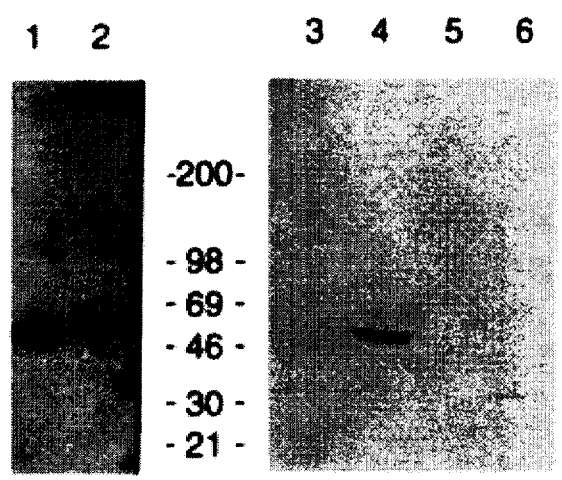

The importance of amino acids 57–64 for LPS-binding suggested that this domain could be the site of interaction between neutralizing mAbs against CD14. Since mAb 3C10 was used to withdraw sCD14$_{\Delta 57-64}$ from CM (FIG. 3), we reasoned that 3C10 must recognize an epitope outside amino acids 57–64. This was confirmed in a BIAcore analysis in which we observed a signal indicative of binding upon adding sCD14$_{\Delta 57-64}$ to immobilized 3C10 (FIG. 7A, compare signal at 0 second to that at 480 sec). We used further BIAcore analysis to test whether a different neutralizing mAb, MEM-18, could interact with the bound sCD14$_{\Delta 57-64}$. However, no binding of MEM-18 was observed to sCD14$_{\Delta 57-64}$ (FIG. 7A, compare signal at 480 sec to that at 800 sec). To confirm this result, we used Western blot analysis. While MEM-18 bound immobilized sCD14$_{1-348}$, it failed to bind sCD14$_{\Delta 57-64}$ (FIG. 7B). Parallel studies performed with polyclonal anti-CD14 confirmed the presence of sCD14$_{\Delta 57-64}$ on the nitrocellulose membrane. These results suggest that MEM-18 recognizes an epitope in the region of amino acids 57–64.

Figure 9:
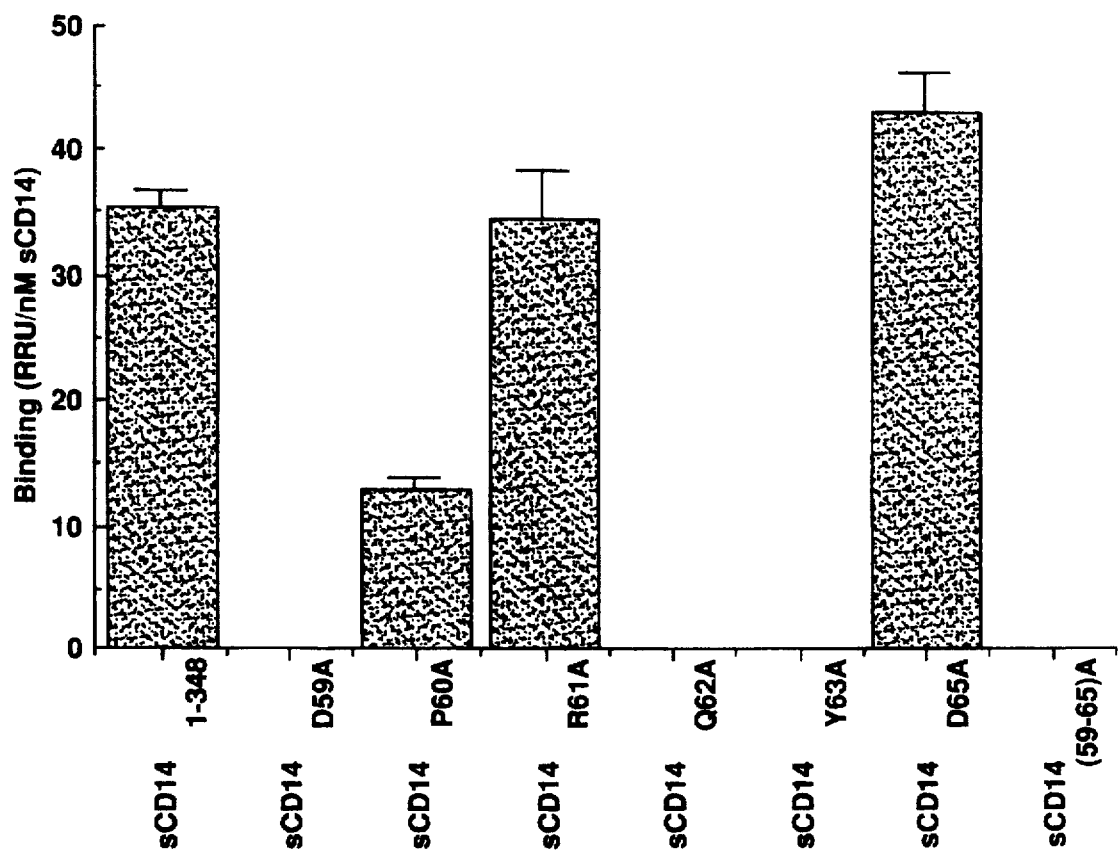
FIG. 9 is a BIAcore analysis of MEM-18 binding to alanine substitution mutants of sCD14. CM containing sCD14$_{1\text{-}348}$ or alanine substitution mutants of sCD14 were analyzed for their ability to bind MEM-18 as described in the Examples. RRU were recorded from four repeats of one experiment and calculated as means ± standard deviation. Binding is expressed as RRU per nM of mutant sCD14 proteins.

In an attempt to further characterize the MEM-18 epitope, we constructed a series of cDNAs encoding sCD14 having alanine substituted at various positions between amino acids 59–65. FIG. 8 summarizes the corresponding amino acid changes in each mutant construct. Mammalian expression vectors containing each mutant cDNA were transiently transfected into COS-7 cells and expression of the mutant protein in CM was monitored by Western blot analysis. No differences in expression of mutant sCD14 proteins were observed in COS-7 CM (data not shown). Therefore, we performed BIAcore analyses to test the ability of each CM containing mutant sCD14 to bind MEM-18. Immobilized mAb 3C10 recognized each of the constructs but sCD14$_{D59A}$, sCD14$_{Q62A}$, sCD14$_{Y63A}$, and sCD14$_{(59-65)A}$ were not recognized by MEM-18 (FIG. 9). Binding of MEM-18 was not affected if Arg$^{61}$ or Asp$^{65}$ was mutated and substitution of alanine at Pro$^{60}$ partially inhibited MEM-18 binding. In summary, we have demonstrated that MEM-18 recognizes an epitope which is minimally comprised of residues Asp$^{59}$, Gln$^{62}$, and Tyr$^{63}$.

Example 6

LPS Competes for the Same Site on CD14 as MEM-18

Figure 10A:
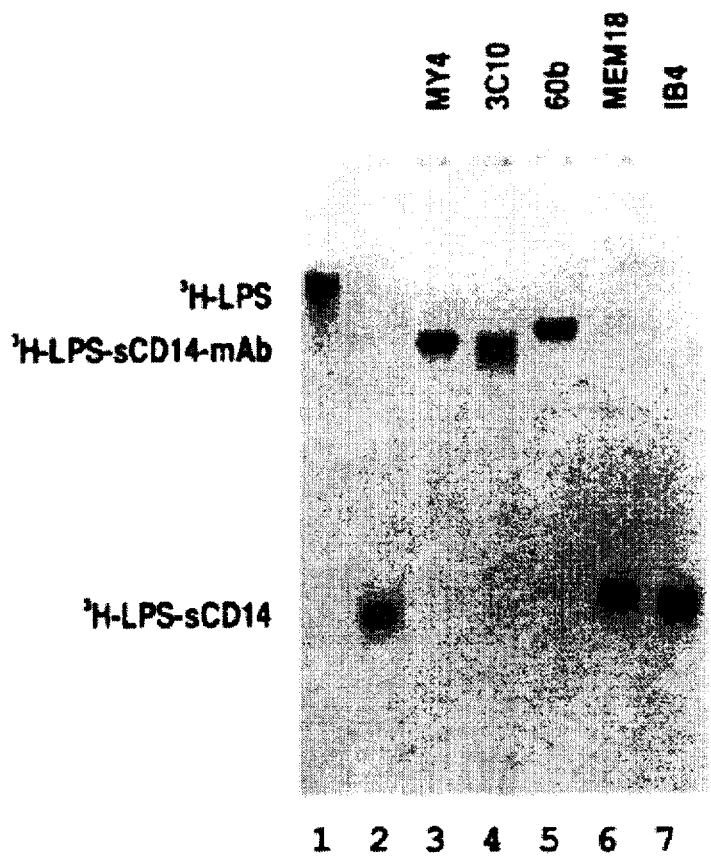
FIGS. 10A and 10B show how LPS competes with mAb MEM-18 for binding to sCD14. 10A. $^3$H-LPS/sCD14 complexes were formed as described in Materials and Methods. Complexes were then diluted 10-fold and incubated with buffer (lane 2) or mAbs MY4, 3C10, MEM-18, or IB4 (lanes 3–7, respectively). The same concentration of $^3$H-LPS was run in the absence of sCD14$_{1\text{-}348}$ for comparison (lane 1). Mixtures were run on 8–16% gels and processed for fluorography. Free $^3$H-LPS, $^3$H-LPS-sCD14, and $^3$H-LPS-sCD14-mAb complexes are indicated. 10B. Purified sCD14$_{1\text{-}348}$ was incubated with mAb MEM18 (lanes 3–11) or 3C10 (lanes 12–13) in the absence of rLBP (lanes 3–7 and 12) or in the presence of rLBP (lanes 8–11, 13) at a concentration of 16.7 nM. Increasing concentrations of LPS (0.25 μg/ml for lanes 4 and 8; 1 μg/ml for lanes 5 and 9; 5 μg/ml for lanes 6 and 10; 25 μg/ml for lanes 7, 11, and 13) were used to competitively inhibit binding of MEM-18 to sCD14$_{1\text{-}348}$. MEM-18 (lane 2) and 3C10 (lane 14) were run without sCD14$_{1\text{-}348}$ to demonstrate the specificity of the antibody used for blotting. Protein mixtures were run on 8–16% native gels and processed for Western blot analysis as indicated in Materials and Methods. Complexes of sCD14$_{1\text{-}348}$-LPS and sCD14$_{1\text{-}348}$-mAb are indicated.
Figure 10B:
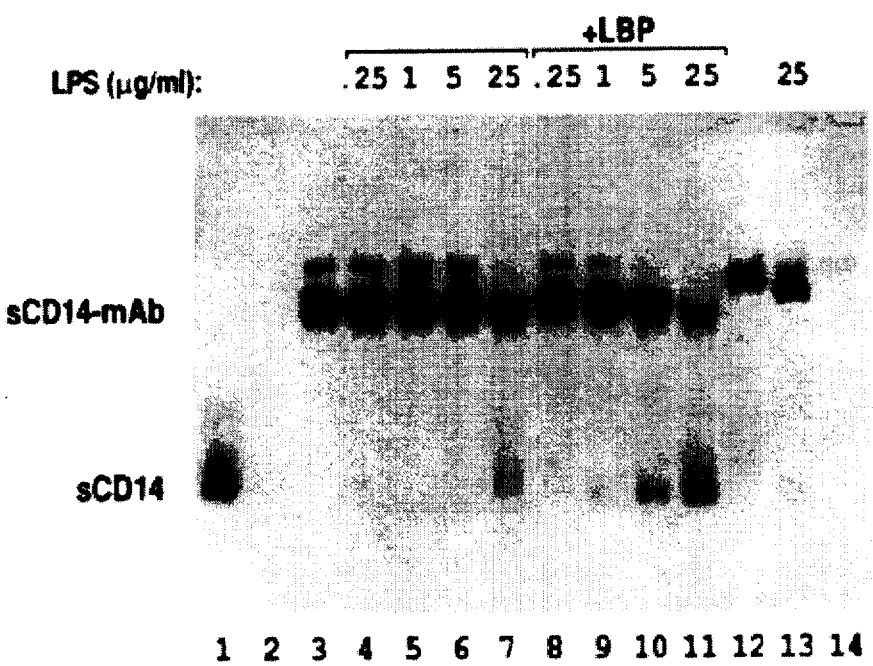

The localization of the MEM-18 epitope to a region we have implicated in LPS-binding suggests that LPS should compete with MEM-18 for binding to sCD14$_{1-348}$. To demonstrate this, we measured the ability of MEM-18 to bind pre-formed LPS-sCD14$_{1-348}$ complexes (FIG. 10A) and the ability of LPS to bind pre-formed sCD14$_{1-348}$-MEM-18 complexes (FIG. 10B). sCD14$_{1-348}$ (FIG. 10B) and complexes of $^3$H-LPS and sCD14$_{1-348}$ (FIG. 10A, lane 2) showed mobility characteristic of a 50-kDa protein and this mobility was not affected by an irrelevant antibody (anti-CD18, FIG. 10A, lane 7). Addition of anti-CD14 mAbs MEM-18, My4, 60b, or 3C10 each caused a quantative "supershift" in the mobility of sCD14$_{1-348}$ to a position consistent with a 250-kDa complex of IgG with two molecules of sCD14$_{1-348}$ (FIG. 10B and data not shown). We further observed that a subset of these mAbs (MY4, 60b, and 3C10) also shifted the mobility of the $^3$H-LPS-sCD14$_{1-348}$ complexes (FIG. 10A). These observations indicate that MY4, 60b, and 3C10 bind to LPS-sCD14$_{1-348}$ complexes and therefore do not compete with LPS for a binding site. In contrast, MEM-18 failed to shift the mobility of $^3$H-LPS in LPS-sCD14$_{1-348}$ complexes (FIG. 10A, lane 6) using conditions that caused complete shifting of sCD14 to the higher molecular weight position in the absence of LPS (FIG. 10B and data not shown). This observation indicates that sCD14$_{1-348}$ cannot simultaneously bind MEM-18 and LPS.

To confirm and extend this observation, complexes of MEM-18 and sCD14$_{1-348}$ were first formed. These complexes showed a mobility characteristic of a 250-kDa protein, confirming the efficacy of MEM-18 in the "supershift" assay (FIG. 10B, lane 3). Addition of increasing doses of LPS to these complexes caused dissociation of the sCD14$_{1-348}$ from the MEM-18 in a dose-dependent fashion. Moreover, the efficacy of LPS in disassociating sCD14$_{1-348}$ from MEM-18 was enhanced by rLBP, a protein that catalytically hastens the binding of LPS to sCD14$_{1-348}$ (Hailman, et al., Ibid. (1994)). LPS did not cause disassociation of sCD14$_{1-348}$ from 3C10 (FIG. 10B), MY4 or 60b (data not shown), confirming that these mAbs do not compete with LPS for binding to sCD14$_{1-348}$. These results further confirm that MEM-18 and LPS bind sCD14$_{1-348}$ in a competitive fashion and may thus recognize overlapping sites.

Example 7

CD14 has an Amphipathic Domain Between Amino Acids 53 and 63

It has been hypothesized (Hoess, A., et al., EMBO J. 12, 3351–3356 (1993)) that Limulus anti-LPS factor (LALF, (Warren, H. S., et al., Infect. Immun. 60, 2506–2513 (1992)), LBP and bactericidal/permeability-increasing (BPI, Gazzano-Santoro, H., et al, Infect. Immun. 60, 4754–4761 (1992)) proteins possess amphipathic domains which are involved in binding LPS. Since the hydrophobic moment (m, Eisenberg, D., Ann. Rev. Biochem. 53, 595–623 (1984)) is directly proportional to amphipathicity, we calculated m throughout CD14 and identified the region having the highest m. Table 1 (see below) compares this region to analogous regions in LALF, LBP, and BPI. The region (amino acids 53–63) having the highest m in CD14 overlaps the site we have identified as being critical for LPS-binding. This region was similar to LALF, LBP, and BPI with respect to its overall pattern of alternating hydrophilic and hydrophobic residues. However, the amphipathic domain in CD14 did differ significantly from the other proteins with respect to its net charge.

TABLE 1

Comparison of region of highest amphipathicity in CD14 and other LPS-binding proteins.

| Protein | Amino acid Sequence[1] | Hydrophobic Moment[2] | Net Change[3] |
|---|---|---|---|
| CD14 | $^{53}$RVDADADPRQY$^{63}$ (SEQ ID NO.24) | 0.83 | −1.09 |
| LALF | $^{32}$RLKWKYKGKFW$^{50}$ | 1.05 | +4.90 |

TABLE 1-continued

Comparison of region of highest amphipathicity in CD14 and other LPS-binding proteins.

| Protein | Amino acid Sequence[1] | Hydrophobic Moment[2] | Net Change[3] |
|---|---|---|---|
| LBP | (SEQ ID NO.25) [86]SIRVQGRWKVR[104] (SEQ ID NO.26) | 1.36 | +3.91 |
| BPI | [86]NIKISGKWKAQ[104] (SEQ ID NO.27) | 1.00 | +2.91 |

[1]Sequences are numbered beginning with the first amino acid of the mature protein. Large, bold-faced letters indicate hydrophilic amino acids.
[2]Hydrophobic moments (for an 11-residue window) were calculated with d = 100° as described (Hoess, A., et al., EMBO J. 12, 3351–3356 (1993)) using a computer program obtained from the laboratory of D. Eisenberg.
[3]Net charge was calculated using a Protean program (DNASTAR, Madison, WI).

Discussion of Examples 1–7

In Examples 1–7, the inventors provide compelling evidence that the region between amino acids 57 and 64 of sCD14 is essential for proper binding of LPS. Deletion of this region abolished the ability of sCD14 to bind LPS in the presence or absence of rLBP. Furthermore, an epitope recognized by neutralizing mAb MEM-18 was mapped to this region and we showed that this mAb competes with LPS for binding to sCD14.

The data also demonstrate the biological consequences of impairing LPS-binding to sCD14. sCD14$_{\Delta 57\text{-}64}$ was inactive in enabling PMN and U373 responses to LPS. These results suggest that binding of LPS to sCD14 is a prerequisite for the biological activity of CD14. This conclusion is consistent with the finding (Hailman, et al., *J. Exp. Med.* 179:269–277 (1994)) that binding of LPS to sCD14$_{1\text{-}348}$ is temporally correlated with biological activity.

Example 8

Preparation of the Peptides of the Invention

The linear polypeptides were synthesized by the solid phase method using either the original t-Boc/benzyl protocol of Merrifield (R. B. Merrifield; *J. Am. Chem. Soc.* (1963), 85, 2149–2154) or using the Fmoc (fluorenyloxycarbonyl) /t-Bu method (L. A. Carpino and G. Y. Hahn; *J.Org.Chem* (1972), 37,3404).

The syntheses were carried out by automated technology using either the Applied Biosystems Inc. 430A or 431A instruments which were programmed with the manufacturer's standard single coupling Fmoc or t-Boc protocols. Preloaded resins, Fmoc and t-Boc protected amino acids and other prepackaged reagents were purchased from Applied Biosystems Inc. (Foster City, Calif.). Cleavage from the resin support and simultaneous side chain deprotection was accomplished by one of two methods depending on which synthetic protocol was used.

Fmoc synthesis: Four hour treatment with 90% trifluoroacetic acid, 2.5% thioanisole, 2.5% 2-mercaptoethanol, 2.5% phenol, 2.5% H$_2$O, followed by concentration and ether precipitation.

T-Boc synthesis: One hour treatment with 95% liquid HF and 5% m-cresol for one hour at 0 degrees Celsius. The HF was removed under reduced pressure and the peptide precipitated with ether.

The crude peptides were purified by high pressure liquid chromatography. Characterization consisted of analytical HPLC, amino acid analysis and electrospray mass spectroscopy.

In addition, synthesis of the following cyclic structure is detailed below to illustrate cyclic peptide synthesis:

[cyclo-S-Ac-Asp-Pro-Arg-Gln-Tyr-Ala-Cys-COOH]

The method used has been previously described by Barker et.al. (P. L. Barker et.al. *J. Med. Chem* (1992), 35, 2040) and Robey and Fields (F. A. Robey and R. L. Fields *Anal.Biochem.* (1989), 177,373)

Synthesis of [cyclo-S-Ac-Asp-Pro-Arg-Gln-Tyr-Ala-Cys-OH]

The sequence H$_2$N-Asp-Pro-Arg-Gln-Tyr-Ala-Cys was assembled by stepwise Fmoc chemistry (as described above) and derivatized with bromoacetic acid and DCC (dicyclohexylcarbodiimide) to form BrAc-Asp-Pro-Arg-Gln-Tyr-Ala-Cys-COOH. The peptide was cleaved from the resin (as above) and cyclized under basic (pH 8) aqueous conditions to form the thioether [cyclo-S-Ac-Asp-Pro-Arg-Gln-Tyr-Ala-Cys-COOH]. The material was purified by preparative HPLC. Mass spectral data (electrospray): expected mass=892 observed: m/e 891 and 892. Analytical HPLC: C-18 column, 5–50% B over 35 mins. Solvent A: 0.1% TFA; solventB 50% 0.1% TFA, 50% acetonitrile) Elution time of [cyclo-S-Ac-Asp-Pro-Arg-Gln-Tyr-Ala-Cys-COOH]=9.78 min.

Example 9

Amino Acid Regions 7–10 and 11–14 are Recognized by Monoclonal Antibody 3C10 as its Epitope on CD14

We have demonstrated that the epitope for the blocking monoclonal antibody 3C10 is located within the first 152 amino acid of CD14. To determine the binding epitope of this monoclonal antibody, we used site-directed mutagenesis to generate a series of CD14 mutants. Each mutant construct has 3 or 4 amino acid residues substituted with alanine. FIG. 11 summarizes the site-directed mutants. The cDNAs encoding these mutants were transfected into COS-7 cells and conditioned media were collected and tested for expression of CD14 mutants. Except for the mutant construct sCD14$_{(18\text{-}21)A}$, which was expressed approximately 20-fold less, all the mutant proteins were expressed at similar levels as determined by Western immunoblot.

Figure 12:
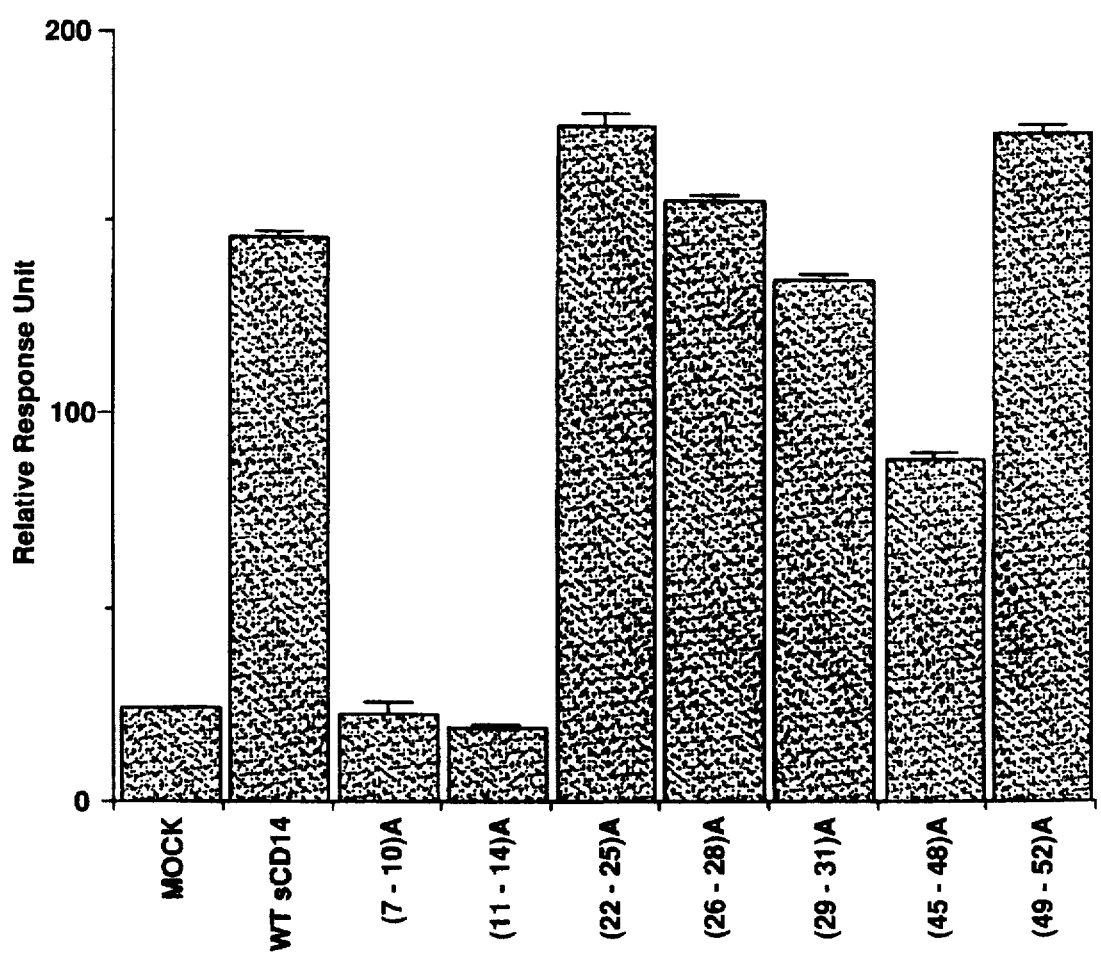
FIG. 12 shows that the monoclonal antibody 3C10 does not recognize CD14 with amino acids 7–10 or 11–14 changed to alanine. Example 9 provides details on how this experiment was conducted.

We tested the ability of these mutant proteins to bind 3C10 by using the BIAcore biosensor instrument, as described above. Monoclonal antibody was immobilized onto a sensor chip in the BIAcore biosensor. Conditioned media containing wildtype sCD14 as well as mutant sCD14 proteins were then injected onto this sensor chip. Binding of sCD14 proteins to immobilized 3C10 will cause a change in the light reflection from the sensor chip and this change was recorded as relative response unit. FIG. 12 shows the relative response units of various constructs. Conditioned media containing no sCD14 (MOCK) shows very little relative response unit. In contrast, injection of conditioned media with sCD14$_{1\text{-}348}$ (WT sCD14) resulted in a relative response unit of about 150. Interestingly, injection of conditioned media with mutants sCD14$_{(7\text{-}10)A}$ or SCD14$_{(11\text{-}14)A}$ did not generate an increase in the relative response unit, suggesting that 3C10 antibody failed to recognize these two mutant proteins. This antibody is capable of binding other mutant constructs as illustrated by FIG. 12. Therefore, we conclude that CD14 amino acid regions 7–10 and 11–14 (i.e., 7–14, inclusive) are recognized by monoclonal antibody 3C10.

Example 10 sCD14$_{(7-10)A}$ is Impaired in Transducing LPS Signal

Figure 13:
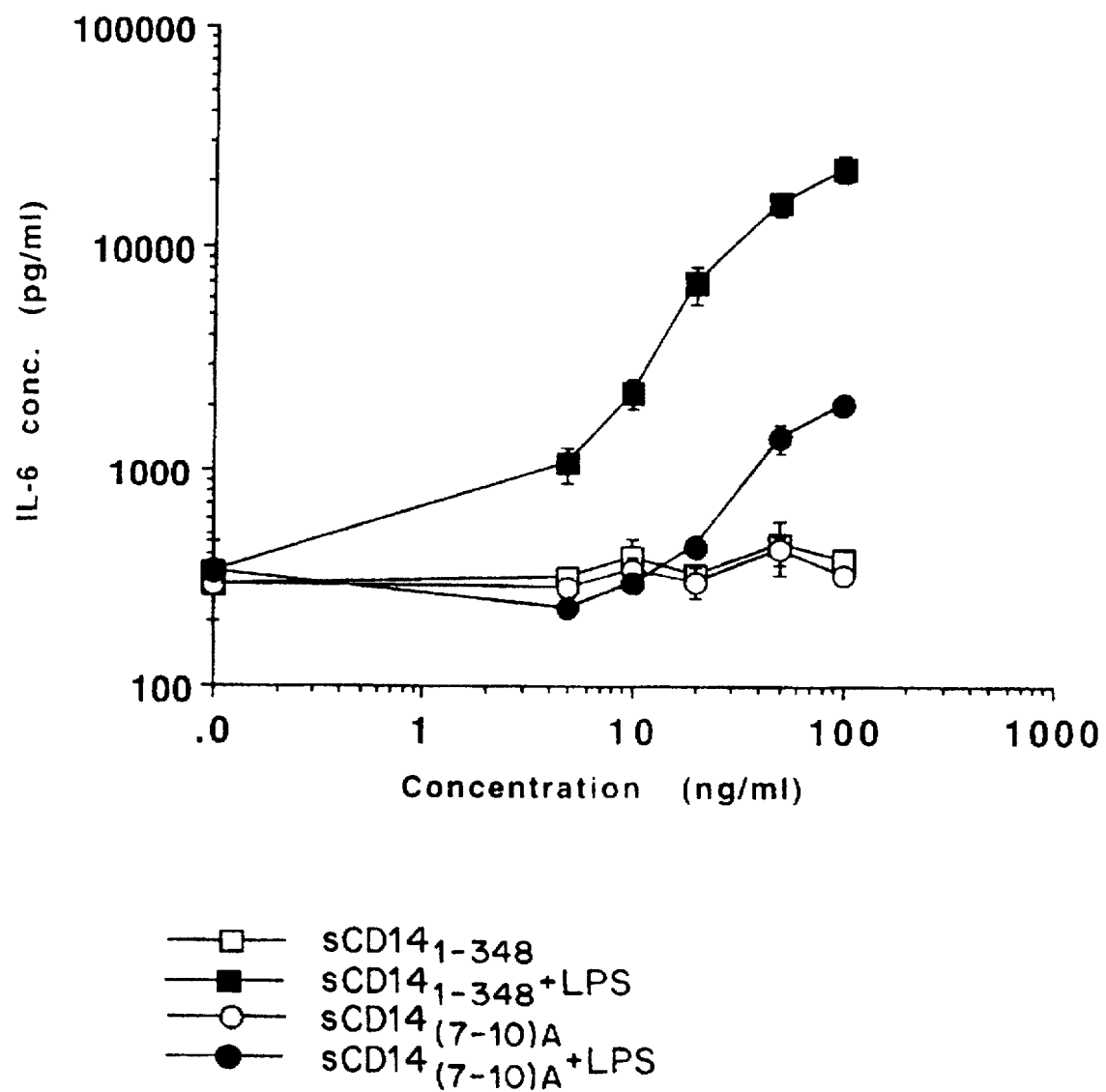
FIG. 13 shows that sCD14$_{(7\text{-}10)A}$ is less capable of inducing IL-6 production in U373 cells than sCD14$_{1\text{-}348}$. U373 cells were treated with various concentrations of sCD14$_{1\text{-}348}$ or sCD14$_{(7\text{-}10)A}$ in the presence or absence of LPS (10 ng/ml) for 24 h. IL-6 levels were determined by IL-6 ELISA. Data presented are means ± deviations from four readings.
Figure 14:
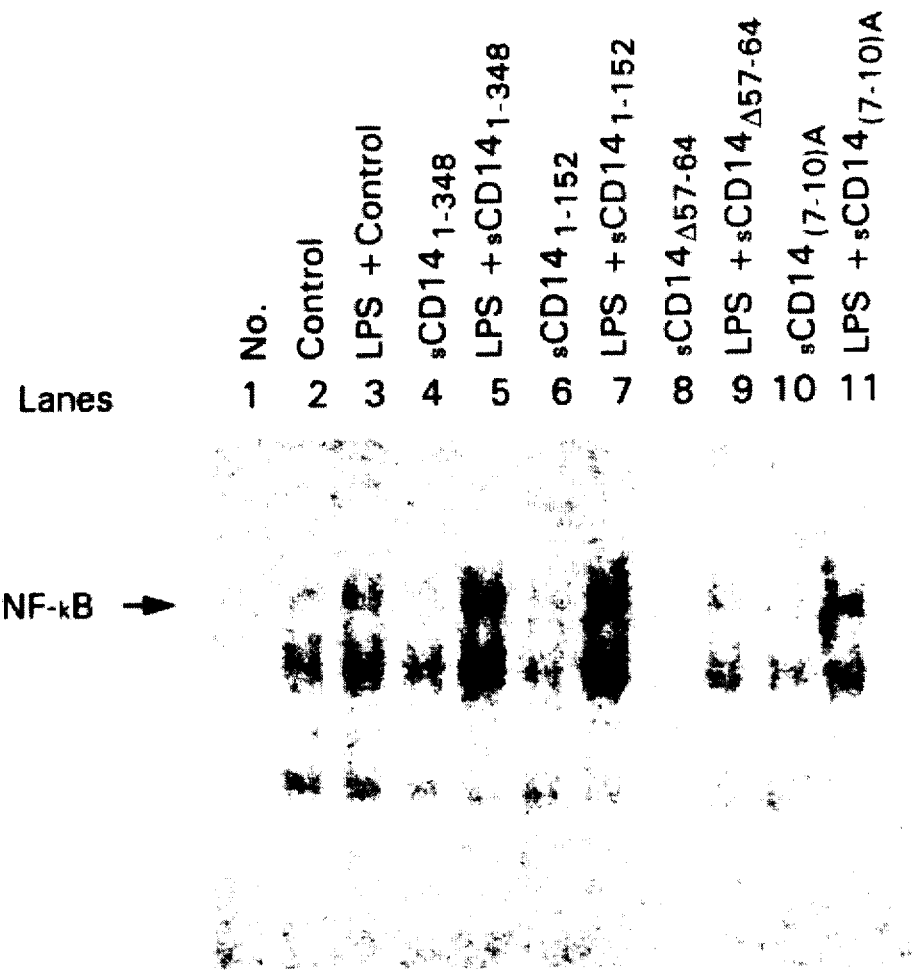
FIG. 14 shows that activation of transcription factor NF-κB is impaired by alanine mutations at amino acid positions 7 to 10. Whole cell extracts (5 μg) from U373 cells treated with no sCD14 (control) or with 20 ng/ml of sCD14$_{1\text{-}348}$, SCD14$_{1\text{-}152}$, sCD14$_{\Delta 57\text{-}64}$, or sCD14$_{(7\text{-}10)A}$ in the presence or absence of LPS (20 ng/ml) were examined for NF-κB binding by electrophoretic mobility shift assay. NF-κB binding site from human immunodeficiency virus long terminal repeat promoter was used as a radioactive probe.

To further determine whether sCD14$_{(7-10)A}$ is capable of transducing LPS signal, we performed massive transient transfections in COS-7 cells and purified this sCD14 mutant to homogeneity from conditioned medium of transfected COS-7 cells. Various concentrations of purified sCD14$_{(7-10)A}$ were used to treat U373 cells in the presence or absence of LPS, and the data are shown in FIG. 13. The ability of inducing IL-6 production by this protein in response to LPS treatment is dramatically decreased as compared to that of wildtype sCD14. This observation strongly suggests that the region of from amino acids 7 to 10 is important for LPS signalling.

We also determined whether mutant sCD14$_{(7-10)A}$ is capable of activating transcription factor NF-κB in U373 cells in response to LPS stimulation. Without sCD14, LPS caused a minor NF-κB activation (compare lanes 2 and 3). Activation of NF-κB is greatly increased when sCD14$_{1-348}$ or sCD14$_{1-152}$ was added in the presence of LPS (lanes 5 and 7). However, this strong induction of NF-κB was not observed when cells were treated with sCD14$_{\Delta 57-64}$ or sCD14$_{(7-10)A}$ (lanes 9 and 11). This example further shows the critical role in LPS of the region between amino acids 7 to 10 in transducing LPS signal into cells.

Example 11 sCD14(7-10)A is Able to Form A Stable Complex with $^3$H-LPS

Figure 15:
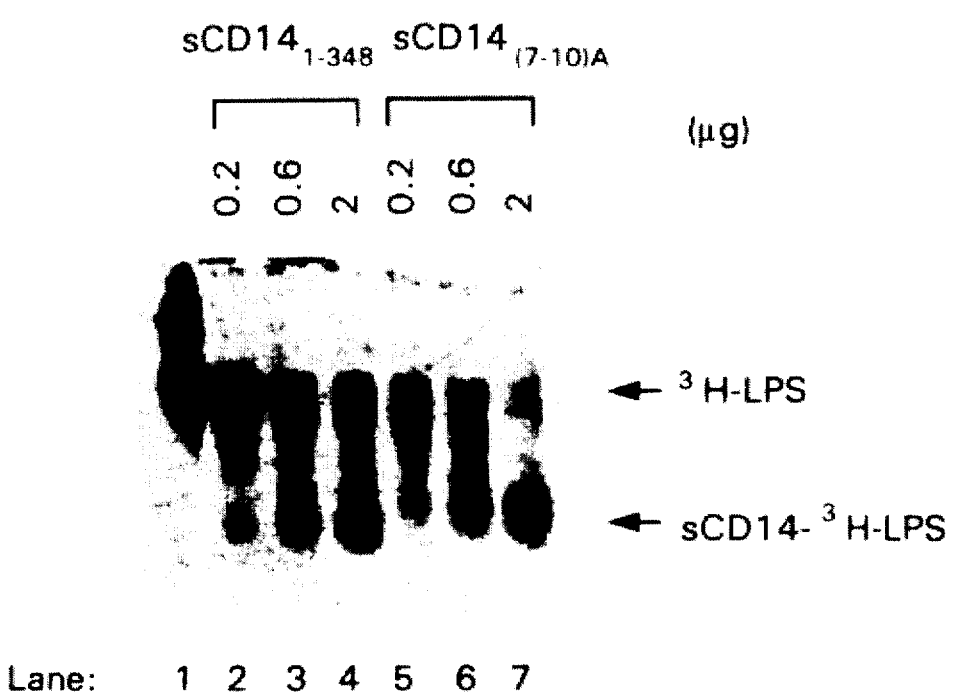
FIG. 15 shows that mutant sCD14$_{(7\text{-}10)A}$ is capable of binding $^3$H-LPS. Various concentrations of sCD14$_{1\text{-}348}$ (lanes 2–4) or sCD14$_{(7\text{-}10)A}$ (lanes 5–7) were incubated with 0.1 µg of ³H-LPS at 37° C. for 30 min. Lane 1 contains LPS in the absence of additional protein. Mixtures were run on 4–20% native polyacrylamide gels and processed for fluorography. Positions of uncomplexed LPS and complexes between LPS and sCD14$_{1-348}$ are indicated.

To determine whether mutant sCD14(7-10)A is capable of binding LPS and further confirm that the region from amino acids 7 to 10 is important for transducing LPS signal but not involved in LPS binding, we performed a native PAGE assay to detect a stable complex between sCD14$_{1-348}$ or SCD14$_{(7-10)A}$ and $^3$H-LPS. Incubation of sCD14$_{1-348}$ or SCD14$_{(7-10)A}$ with $^3$H-LPS leads to the formation of stable complexes of sCD14-$^3$H-LPS (FIG. 15). This data demonstrates that sCD14$_{(7-10)A}$ is able to bind LPS and that the region from amino acids 7 to 10, which is important for LPS signalling, is not involved in LPS binding.

Example 12

Gram Positive Cell Components Compete with LPS for Binding to sCD14

Figure 16:
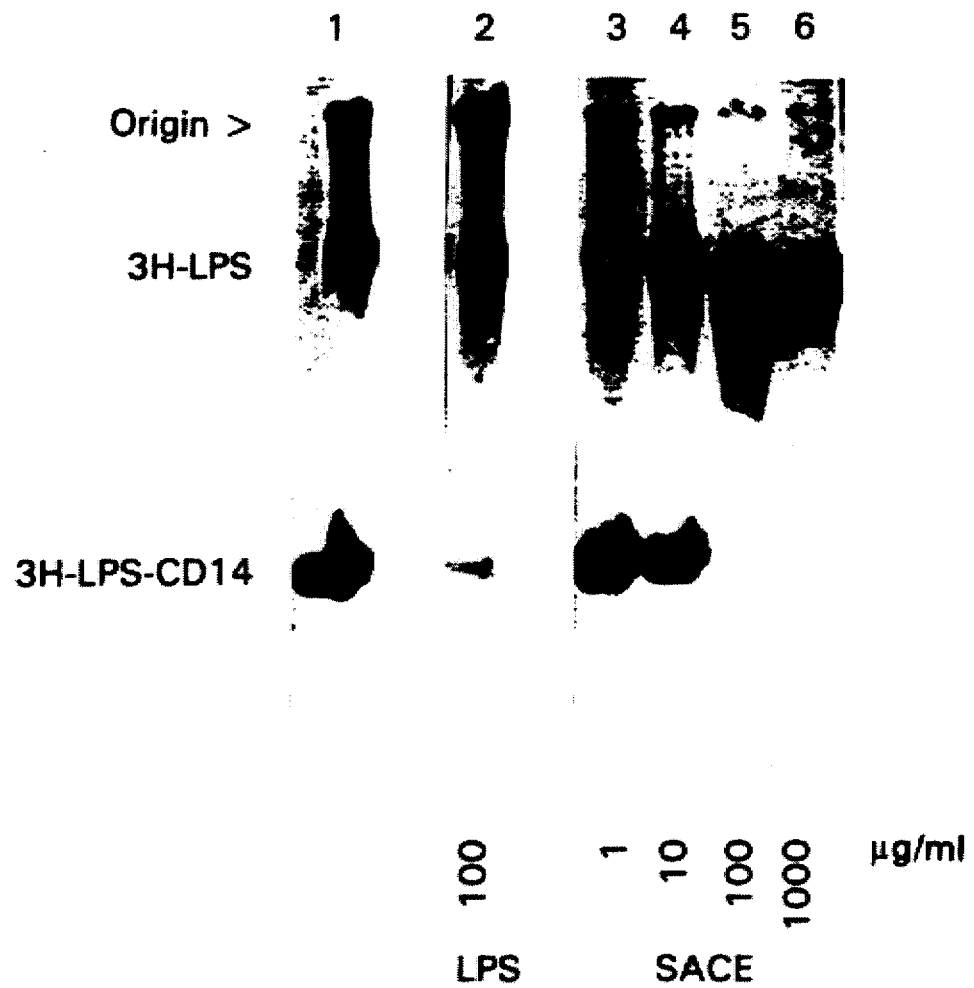
FIG. 16 shows that an extract of gram positive bacteria (SACE) inhibits the binding of ³H-LPS to sCD14. ³H-LPS (1 µg/ml) and sCD14 (50 µg/ml) were incubated alone (lane 1) or with unlabeled LPS (lane 2) or *Staphylococcus aureus* crude extract (SACE, lanes 3–6) at 37° for 17 hrs in PBS containing 1 mM EDTA. The samples were then run on a native polyacrylamide gel, and radioactivity was detected by radioautography. Binding of ³H-LPS to sCD14 was inhibited both by unlabeled and by SACE.

FIG. 16 presents the evidence that a gram-positive molecule present in the phenol extract of *S. aureus* (SACE) can bind to sCD14 and compete with LPS for a binding site. Other data (not shown) indicates that SACE strongly stimulates cells in a CD14-dependent fashion. The binding site(s) now defined on CD14 may be relevant not only to responses initiated by gram-negative but also by gram-positive bacteria.

Abbreviations

The abbreviations used in the Examples section above are: BCIP, 5-bromo-4-chloro-3-indoyl phosphate-toluidine salt; BPI, bactericidal/permeability-increasing protein; CHO, Chinese hamster ovary; CD, circular dichroism; CM, conditioned medium; HBSS, Hank's balanced salt solution; IL-6, interleukin-6; LALF, Limulus anti-LPS factor; LBP, LPS-binding protein; LPS, lipopolysaccharide; NBT, p-nitro blue tetrazolium chloride; PAGE, polyacrylamide gel electrophoresis; PBS, phosphate-buffered saline; PMN, polymorphonuclear leukocyte; r, recombinant; RU, response unit; sCD14, soluble CD14; ELISA, enzyme linked immunosorbant assay.

The invention now being fully described, it will be apparent to one of ordinary skill in the art that many changes and modifications can be made thereto, without departing from the spirit and scope of the invention as set forth herein.

The embodiments of the invention in which an exclusive property or privilege is claimed are defined as follows:

1. A linear or cyclic peptide consisting of 8 to 60 amino acid residues comprising the amino acid sequence of SEQ ID NO:46, wherein $X_1$ is selected from the group consisting of Asp and Glu;
$X_2$ is selected from the group consisting of Ala and Ser;
$X_3$ is selected from the group consisting of Asp and Glu;
$X_4$ is selected from the group consisting of Pro and Gly;
$X_5$ is selected from the group consisting of Arg and Lys;
$X_6$ is selected from the group consisting of Gln, Asn and His;
$X_7$ is selected from the group consisting of Tyr, Trp and Phe;
$X_8$ is selected from the group consisting of Ala and Ser; and physiologically acceptable salts thereof;
wherein said peptide binds to lipopolysaccharide (LPS), and with the proviso that when the peptide comprises the amino acid sequence Asp-Ala-Asp-Pro-Arg-Gln-Tyr-Ala (SEQ ID NO:1), then the peptide has only 8 to 12 amino acids residues in total.

2. A peptide according to claim 1 which has from 8 to 20 amino acids.

3. A peptide according to claim 1 which has 8 to 10 amino acids.

4. A peptide according to claim 1 which further comprises from 1 to 5 amino acids on each of the N and C termini of said amino acid sequence, wherein said 1 to 5 amino acids correspond to the amino acids that occur on either side of amino acids 57 to 64 of native CD14.

5. A peptide according to claim 1 consisting of 8 to 12 amino acid residues and comprising the sequence: Asp-Ala-Asp-Pro-Arg-Gln-Tyr-Ala (SEQ ID NO:1), and physiologically acceptable salts thereof.

6. A peptide according to claim 5 consisting of the sequence: Asp-Ala-Asp-Pro-Arg-Gln-Tyr-Ala (SEQ ID NO: 1), and physiologically acceptable salts thereof.

7. A peptide comprising the following amino acid sequence:

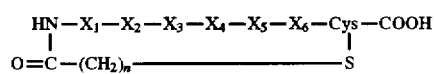

wherein, $X_1$ is selected from the group consisting of Asp and Glu;
$X_2$ is selected from the group consisting of Pro and Gly;
$X_3$ is selected from the group consisting of Arg and Lys;
$X_4$ is selected from the group consisting of Gln, Asn and His;
$X_5$ is selected from the group consisting of Tyr, Trp and Phe;
$X_6$ is selected from the group consisting of Ala and Ser; and physiologically acceptable salts thereof;

n is from 1 to 3; and further wherein said peptide binds to lipopolysaccharide.

8. A peptide according to claim 7 which is:

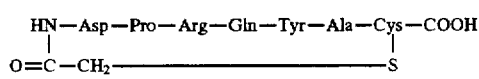

and physiologically acceptable salts thereof.

9. A peptide comprising the following amino acid sequence:

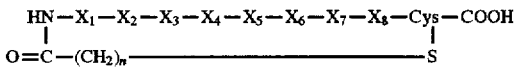

wherein, $X_1$ is selected from the group consisting of Ala and Ser;

$X_2$ is selected from the group consisting of Asp and Glu;

$X_3$ is selected from the group consisting of Pro and Gly;

$X_4$ is selected from the group consisting of Arg and Lys;

$X_5$ is selected from the group consisting of Gln, Asn and His;

$X_6$ is selected from the group consisting of Tyr, Trp and Phe;

$X_7$ is selected from the group consisting of Ala and Ser;

$X_8$ is selected from the group consisting of Asp and Glu;

n is from 1 to 3; and physiologically acceptable salts thereof; and further wherein said peptide binds to lipopolysaccharide.

10. A peptide according to claim 7 which is:

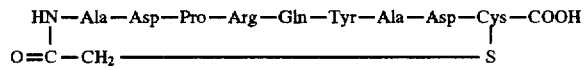

and physiologically acceptable salts thereof.

11. A peptide comprising the following amino acid sequence:

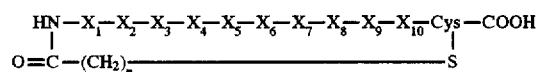

wherein, $X_1$ is selected from the group consisting of Asp and Glu;

$X_2$ is selected from the group consisting of Ala and Ser;

$X_3$ is selected from the group consisting of Asp and Glu;

$X_4$ is selected from the group consisting of Pro and Gly;

$X_5$ is selected from the group consisting of Arg and Lys;

$X_6$ is selected from the group consisting of Gln, Asn and His;

$X_7$ is selected from the group consisting of Tyr, Trp and Phe;

$X_8$ is selected from the group consisting of Ala and Ser;

$X_9$ is selected from the group consisting of Asp and Glu;

$X_{10}$ is selected from the group consisting of Thr and Ser;

n is from 1 to 3; and physiologically acceptable salts thereof; and further wherein said peptide binds to lipopolysaccharide.

12. A peptide according to claim 7 which is:

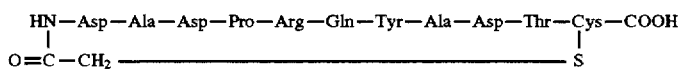

and physiologically acceptable salts thereof.

13. A peptide comprising the following amino acid sequence:

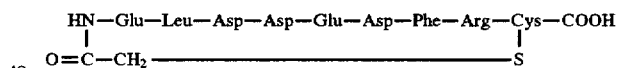

wherein, n is from 1 to 3; and physiologically acceptable salts thereof.

14. A peptide comprising the following amino acid sequence:

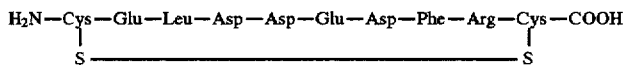

and physiologically acceptable salts thereof.

15. A method of treating a lipopolysaccharide-mediated inflammatory condition in a patient in need thereof, which comprises administering to said patient an effective amount of a peptide selected from the peptide of any of claims 1–14.

16. A method according to claim 15, wherein said amount is from 0.1 mg/kg to 100 mg/kg.

17. A pharmaceutical composition comprising a peptide according to any one of claims 1–14, and a pharmaceutically acceptable carrier.

* * * * *

UNITED STATES PATENT AND TRADEMARK OFFICE
CERTIFICATE OF CORRECTION

PATENT NO. : 5,766,593
DATED : June 16, 1998
INVENTOR : Lichenstein et al.

It is certified that error appears in the above-identified patent and that said Letters Patent is hereby corrected as shown below:

Title page, column 2 [56] OTHER PUBLICATIONS, McGinley et al., change "(1950" to --1995--.

Column 7, line 66, after "FIG 8" add --SEQ ID NOs:28-35--.

Column 8, line 32, after "sCD14" add --SEQ ID NO:36--.

Column 8, line 60, change "SCD14$_{1-152}$" to --sCD14$_{1-152}$--.

Column 26, line 60, change "SCD14$_{(11-14)A}$" to -- sCD14$_{(11-14)A}$--.

Column 28, line 1, change "SCD14$_{(7-10)A}$" to -- sCD14$_{(7-10)A}$--.

Column 28, line 2, change "SCD14$_{(7-10)A}$" to -- sCD14$_{(7-10)A}$--.

Column 41-42, SEQ ID NO:32, replace "Arg Val Asp Ala Asp Ala Asp Pro Arg Gln Ala Ala Asp Thr Val Lys" with --Arg Val Asp Ala Asp Ala Asp Pro Arg Ala Tyr Ala Asp Thr Val Lys--.

Column 56, line 42, delete "wherein, n is from 1 to 3;"

Signed and Sealed this

Twenty-ninth Day of December, 1998

*Attest:*

BRUCE LEHMAN

*Attesting Officer*      *Commissioner of Patents and Trademarks*

UNITED STATES PATENT AND TRADEMARK OFFICE
CERTIFICATE OF CORRECTION

PATENT NO.    : 5,766,593
DATED         : June 16, 1998
INVENTOR      : Lichenstein et al.

It is certified that error appears in the above-identified patent and that said Letters Patent is hereby corrected as shown below:

On the title page: Item

[73] Assignee:, add --The Rockefeller University, New York, NY--.

Signed and Sealed this

Fourteenth Day of September, 1999

Attest:

Q. TODD DICKINSON

*Attesting Officer*          *Acting Commissioner of Patents and Trademarks*

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Asp Ala Asp Pro Arg Gln Tyr Ala
    1                     5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown (i i) MOLECULE TYPE: protein (i x) FEATURE:
    (A) NAME/KEY: Modified-site
    (B) LOCATION: 1..7
    (D) OTHER INFORMATION: /note= "Amino acids 1 and 7 are
        linked via - CO-CH2-S-"

(x i) SEQUENCE DESCRIPTION: SEQ ID NO:2:

Asp Pro Arg Gln Tyr Ala Cys
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (i i) MOLECULE TYPE: protein (i x) FEATURE:
        (A) NAME/KEY: Modified-site
        (B) LOCATION: 1..9
        (D) OTHER INFORMATION: /note= "Amino acids 1 and 9 are
            linked together via -CO-CH2-S-"

(x i) SEQUENCE DESCRIPTION: SEQ ID NO:3:

Ala Asp Pro Arg Gln Tyr Ala Asp Cys
1               5

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: unknown
        (D) TOPOLOGY: unknown (i i) MOLECULE TYPE: protein (i x) FEATURE:
        (A) NAME/KEY: Modified-site
        (B) LOCATION: 1..11
        (D) OTHER INFORMATION: /note= "Amino acids 1 and 11 are
            linked together via -CO-CH2-S-"

(x i) SEQUENCE DESCRIPTION: SEQ ID NO:4:

Asp Ala Asp Pro Arg Gln Tyr Ala Asp Thr Cys
1               5                       10

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: unknown
        (D) TOPOLOGY: unknown (i i) MOLECULE TYPE: protein (i x) FEATURE:
        (A) NAME/KEY: Modified-site
        (B) LOCATION: 1..9
        (D) OTHER INFORMATION: /note= "Amino acids 1 and 9 are
            linked together via -CO-(CH2)n-S-"

(x i) SEQUENCE DESCRIPTION: SEQ ID NO:5:

Glu Leu Asp Asp Glu Asp Phe Arg Cys
1               5

( 2 ) INFORMATION FOR SEQ ID NO:6:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Disulfide-bond
        ( B ) LOCATION: 1..10

( x i ) SEQUENCE DESCRIPTION: SEQ ID NO:6:

```
Cys  Glu  Leu  Asp  Asp  Glu  Asp  Phe  Arg  Cys
1                    5                        10
```

( 2 ) INFORMATION FOR SEQ ID NO:7:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Asp  Ala  Asp  Pro  Arg  Gln  Tyr  Ala
1                    5
```

( 2 ) INFORMATION FOR SEQ ID NO:8:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Asp  Ala  Glu  Pro  Arg  Gln  Tyr  Ala
1                    5
```

( 2 ) INFORMATION FOR SEQ ID NO:9:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Asp  Ala  Glu  Pro  Arg  Asn  Tyr  Ala
1                    5
```

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

Asp Ala Glu Pro Arg Gln Phe Ala
1               5

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Asp Ala Glu Pro Arg Asn Phe Ala
1               5

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

Asp Ala Asp Pro Arg Asn Tyr Ala
1               5

(2) INFORMATION FOR SEQ ID NO:13:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

Asp Ala Asp Pro Arg Asn Phe Ala
1               5

(2) INFORMATION FOR SEQ ID NO:14:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:14:

Asp Ala Asp Pro Arg Gln Phe Ala
1               5

(2) INFORMATION FOR SEQ ID NO:15:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:15:

Glu Leu Asp Asp Glu Asp Phe Arg
1               5

( 2 ) INFORMATION FOR SEQ ID NO:16:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:16:

TAAAGCGCGT CGATGCGGAC ACGGTCAAGG CTCTCC     36

( 2 ) INFORMATION FOR SEQ ID NO:17:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:17:

GATGCGGACG CCGCCCCTAG GCAGTATGCT GACACG     36

( 2 ) INFORMATION FOR SEQ ID NO:18:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:18:

GATGCGGACG CCGACGCGCG GCAGTATGCT GAC     33

( 2 ) INFORMATION FOR SEQ ID NO:19:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:19:

GCGGACGCCG ACCCTGCGCA GTATGCTGAC AC     32

( 2 ) INFORMATION FOR SEQ ID NO:20:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:20:

GACGCCGACC CGCGAGCGTA TGCTGACACG GTC     33

( 2 ) INFORMATION FOR SEQ ID NO:21:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

CGCCGACCCG CGTCAGGCTG CTGACACGGT TCAAG                            35

( 2 ) INFORMATION FOR SEQ ID NO:22:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:22:

CCGCGGCAGT ATGCTGCCAC GGTCAAGGCT CTCC                             34

( 2 ) INFORMATION FOR SEQ ID NO:23:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: protein ( x i ) SEQUENCE DESCRIPTION: SEQ ID NO:23:

GTCGATGCGG ACGCCGCCGC GGCGGCGGCT GCTGCCACGG TCAAGGCTCT CCGC      54

( 2 ) INFORMATION FOR SEQ ID NO:24:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:24:

```
Arg  Val  Asp  Ala  Asp  Ala  Asp  Pro  Arg  Gln  Tyr
 1              5                        10
```

( 2 ) INFORMATION FOR SEQ ID NO:25:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Arg  Leu  Lys  Trp  Lys  Tyr  Lys  Gly  Lys  Phe  Trp
 1              5                        10
```

( 2 ) INFORMATION FOR SEQ ID NO:26:

( i ) SEQUENCE CHARACTERISTICS:

( A ) LENGTH: 11 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:26:

Ser Ile Arg Val Gln Gly Arg Trp Lys Val Arg
1               5                   10

( 2 ) INFORMATION FOR SEQ ID NO:27:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:27:

Asn Ile Lys Ile Ser Gly Lys Trp Lys Ala Gln
1               5                   10

( 2 ) INFORMATION FOR SEQ ID NO:28:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:28:

Arg Val Asp Ala Asp Ala Asp Pro Arg Gln Tyr Ala Asp Thr Val Lys
1               5                   10                  15

( 2 ) INFORMATION FOR SEQ ID NO:29:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:29:

Arg Val Asp Ala Asp Ala Ala Pro Arg Gln Tyr Ala Asp Thr Val Lys
1               5                   10                  15

( 2 ) INFORMATION FOR SEQ ID NO:30:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:30:

Arg Val Asp Ala Asp Ala Asp Ala Arg Gln Tyr Ala Asp Thr Val Lys
1               5                   10                  15

( 2 ) INFORMATION FOR SEQ ID NO:31:

( i ) SEQUENCE CHARACTERISTICS:

( A ) LENGTH: 16 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:31:

Arg Val Asp Ala Asp Ala Asp Pro Ala Gln Tyr Ala Asp Thr Val Lys
1               5                   10                  15

( 2 ) INFORMATION FOR SEQ ID NO:32:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:32:

Arg Val Asp Ala Asp Ala Asp Pro Arg Gln Ala Ala Asp Thr Val Lys
1               5                   10                  15

( 2 ) INFORMATION FOR SEQ ID NO:33:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:33:

Arg Val Asp Ala Asp Ala Asp Pro Arg Gln Ala Ala Asp Thr Val Lys
1               5                   10                  15

( 2 ) INFORMATION FOR SEQ ID NO:34:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:34:

Arg Val Asp Ala Asp Ala Asp Pro Arg Gln Tyr Ala Ala Thr Val Lys
1               5                   10                  15

( 2 ) INFORMATION FOR SEQ ID NO:35:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO:35:

Arg Val Asp Ala Asp Ala Ala Ala Ala Ala Ala Ala Ala Thr Val Lys
1               5                   10                  15

( 2 ) INFORMATION FOR SEQ ID NO:36:

( i ) SEQUENCE CHARACTERISTICS:

(A) LENGTH: 55 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:36:

```
Thr Thr Pro Glu Pro Cys Glu Leu Asp Asp Glu Asp Phe Arg Cys Val
1               5                   10                  15
Cys Asn Phe Ser Glu Pro Gln Pro Asp Trp Ser Glu Ala Phe Gln Cys
                20                  25                  30
Val Ser Ala Val Glu Val Glu Ile His Ala Gly Gly Leu Asn Leu Glu
                35                  40                  45
Pro Phe Leu Lys Arg Val Asp
                50              55
```

(2) INFORMATION FOR SEQ ID NO:37:

(i) SEQUENCE CHARACTERISTICS:
(A) LENGTH: 55 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:37:

```
Thr Thr Pro Glu Pro Cys Ala Ala Ala Ala Glu Asp Phe Arg Cys Val
1               5                   10                  15
Cys Asn Phe Ser Glu Pro Gln Pro Asp Trp Ser Glu Ala Phe Gln Cys
                20                  25                  30
Val Ser Ala Val Glu Val Glu Ile His Ala Gly Gly Leu Asn Leu Glu
                35                  40                  45
Pro Phe Leu Lys Arg Val Asp
                50              55
```

(2) INFORMATION FOR SEQ ID NO:38:

(i) SEQUENCE CHARACTERISTICS:
(A) LENGTH: 55 amino acids
(B) TYPE: amino acid
(C) STRANDEDNESS: single
(D) TOPOLOGY: linear (ii) MOLECULE TYPE: protein (xi) SEQUENCE DESCRIPTION: SEQ ID NO:38:

```
Thr Thr Pro Glu Pro Cys Glu Leu Asp Asp Ala Ala Ala Ala Cys Val
1               5                   10                  15
Cys Asn Phe Ser Glu Pro Gln Pro Asp Trp Ser Glu Ala Phe Gln Cys
                20                  25                  30
Val Ser Ala Val Glu Val Glu Ile His Ala Gly Gly Leu Asn Leu Glu
                35                  40                  45
Pro Phe Leu Lys Arg Val Asp
                50              55
```

(2) INFORMATION FOR SEQ ID NO:39:

(i) SEQUENCE CHARACTERISTICS:
(A) LENGTH: 55 amino acids
(B) TYPE: amino acid
(C) STRANDEDNESS: single
(D) TOPOLOGY: linear ( i i ) MOLECULE TYPE: protein ( x i ) SEQUENCE DESCRIPTION: SEQ ID NO:39:

```
Thr Thr Pro Glu Pro Cys Glu Leu Asp Asp Glu Asp Phe Arg Cys Val
1               5                   10                  15
Cys Ala Ala Ala Ala Pro Gln Pro Asp Trp Ser Glu Ala Phe Gln Cys
              20                  25                  30
Val Ser Ala Val Glu Val Glu Ile His Ala Gly Gly Leu Asn Leu Glu
              35                  40                  45
Pro Phe Leu Lys Arg Val Asp
              50                  55
```

( 2 ) INFORMATION FOR SEQ ID NO:40:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:40:

```
Thr Thr Pro Glu Pro Cys Glu Leu Asp Asp Glu Asp Phe Arg Cys Val
1               5                   10                  15
Cys Asn Phe Ser Glu Ala Ala Ala Trp Ser Glu Ala Phe Gln Cys
              20                  25                  30
Val Ser Ala Val Glu Val Glu Ile His Ala Gly Gly Leu Asn Leu Glu
              35                  40                  45
Pro Phe Leu Lys Arg Val Asp
              50                  55
```

( 2 ) INFORMATION FOR SEQ ID NO:41:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:41:

```
Thr Thr Pro Glu Pro Cys Glu Leu Asp Asp Glu Asp Phe Arg Cys Val
1               5                   10                  15
Cys Asn Phe Ser Glu Pro Gln Pro Asp Ala Ala Ala Ala Phe Gln Cys
              20                  25                  30
Val Ser Ala Val Glu Val Glu Ile His Ala Gly Gly Leu Asn Leu Glu
              35                  40                  45
Pro Phe Leu Lys Arg Val Asp
              50                  55
```

( 2 ) INFORMATION FOR SEQ ID NO:42:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:42:

```
Thr Thr Pro Glu Pro Cys Glu Leu Asp Asp Glu Asp Phe Arg Cys Val
```

```
              1                         5                              10                           15
           Cys  Asn  Phe  Ser  Glu  Pro  Gln  Pro  Asp  Trp  Ser  Glu  Ala  Phe  Gln  Cys
                          20                       25                       30
           Val  Ser  Ala  Val  Glu  Val  Glu  Ile  His  Ala  Gly  Gly  Ala  Ala  Ala  Ala
                          35                       40                       45
           Pro  Phe  Leu  Lys  Arg  Val  Asp
                50                       55
```

( 2 ) INFORMATION FOR SEQ ID NO:43:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:43:

```
           Thr  Thr  Pro  Glu  Pro  Cys  Glu  Leu  Asp  Asp  Glu  Asp  Phe  Arg  Cys  Val
            1                   5                       10                       15
           Cys  Asn  Phe  Ser  Glu  Pro  Gln  Pro  Asp  Trp  Ser  Glu  Ala  Phe  Gln  Cys
                          20                       25                       30
           Val  Ser  Ala  Val  Glu  Val  Glu  Ile  His  Ala  Gly  Gly  Ala  Ala  Ala  Ala
                          35                       40                       45
           Pro  Phe  Leu  Lys  Arg  Val  Asp
                50                       55
```

( 2 ) INFORMATION FOR SEQ ID NO:44:

( i ) SEQUENCE CHARACTERISTICS:
        ( A ) LENGTH: 55 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:44:

```
           Thr  Thr  Pro  Glu  Pro  Cys  Glu  Leu  Asp  Asp  Glu  Asp  Phe  Arg  Cys  Val
            1                   5                       10                       15
           Cys  Asn  Phe  Ser  Glu  Pro  Gln  Pro  Asp  Trp  Ser  Glu  Ala  Phe  Gln  Cys
                          20                       25                       30
           Val  Ser  Ala  Val  Glu  Val  Glu  Ile  His  Ala  Gly  Gly  Leu  Asn  Leu  Glu
                          35                       40                       45
           Ala  Ala  Ala  Ala  Arg  Val  Asp
                50                       55
```

( 2 ) INFORMATION FOR SEQ ID NO:45:

( i ) SEQUENCE CHARACTERISTICS:
        ( A ) LENGTH: 348 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:45:

```
           Thr  Thr  Pro  Glu  Pro  Cys  Glu  Leu  Asp  Asp  Glu  Asp  Phe  Arg  Cys  Val
            1                   5                       10                       15
           Cys  Asn  Phe  Ser  Glu  Pro  Gln  Pro  Asp  Trp  Ser  Glu  Ala  Phe  Gln  Cys
                          20                       25                       30
```

-continued

| | | | | | | | | | | | | | |
|---|---|---|---|---|---|---|---|---|---|---|---|---|---|
| Val | Ser | Ala | Val | Glu | Val | Glu | Ile | His | Ala | Gly | Gly | Leu | Asn | Leu | Glu |
| | | 35 | | | | 40 | | | | | | 45 | | | |
| Pro | Phe | Leu | Lys | Arg | Val | Asp | Ala | Asp | Ala | Asp | Pro | Arg | Gln | Tyr | Ala |
| | | 50 | | | | 55 | | | | | 60 | | | | |
| Asp | Thr | Val | Lys | Ala | Leu | Arg | Val | Arg | Arg | Leu | Thr | Val | Gly | Ala | Ala |
| 65 | | | | | 70 | | | | | 75 | | | | | 80 |
| Gln | Val | Pro | Ala | Gln | Leu | Leu | Val | Gly | Ala | Leu | Arg | Val | Leu | Ala | Tyr |
| | | | | 85 | | | | | 90 | | | | | 95 | |
| Ser | Arg | Leu | Lys | Glu | Leu | Thr | Leu | Glu | Asp | Leu | Lys | Ile | Thr | Gly | Thr |
| | | | 100 | | | | | 105 | | | | | 110 | | |
| Met | Pro | Pro | Leu | Pro | Leu | Glu | Ala | Thr | Gly | Leu | Ala | Leu | Ser | Ser | Leu |
| | | 115 | | | | 120 | | | | | 125 | | | | |
| Arg | Leu | Arg | Asn | Val | Ser | Trp | Ala | Thr | Gly | Arg | Ser | Trp | Leu | Ala | Glu |
| | 130 | | | | 135 | | | | | 140 | | | | | |
| Leu | Gln | Gln | Trp | Leu | Lys | Pro | Gly | Leu | Lys | Val | Leu | Ser | Ile | Ala | Gln |
| 145 | | | | | 150 | | | | | 155 | | | | | 160 |
| Ala | His | Ser | Pro | Ala | Phe | Ser | Cys | Glu | Gln | Val | Arg | Ala | Phe | Pro | Ala |
| | | | | 165 | | | | | 170 | | | | | 175 | |
| Leu | Thr | Ser | Leu | Asp | Leu | Ser | Asp | Asn | Pro | Gly | Leu | Gly | Glu | Arg | Gly |
| | | | 180 | | | | | 185 | | | | | 190 | | |
| Leu | Met | Ala | Ala | Leu | Cys | Pro | His | Lys | Phe | Pro | Ala | Ile | Gln | Asn | Leu |
| | | 195 | | | | | 200 | | | | | 205 | | | |
| Ala | Leu | Arg | Asn | Thr | Gly | Met | Glu | Thr | Pro | Thr | Gly | Val | Cys | Ala | Ala |
| | 210 | | | | | 215 | | | | | 220 | | | | |
| Leu | Ala | Ala | Ala | Gly | Val | Gln | Pro | His | Ser | Leu | Asp | Leu | Ser | His | Asn |
| 225 | | | | | 230 | | | | | 235 | | | | | 240 |
| Ser | Leu | Arg | Ala | Thr | Val | Asn | Pro | Ser | Ala | Pro | Arg | Cys | Met | Trp | Ser |
| | | | | 245 | | | | | 250 | | | | | 255 | |
| Ser | Ala | Leu | Asn | Ser | Leu | Asn | Leu | Ser | Phe | Ala | Gly | Leu | Glu | Gln | Val |
| | | | 260 | | | | | 265 | | | | | 270 | | |
| Pro | Lys | Gly | Leu | Pro | Ala | Lys | Leu | Arg | Val | Leu | Asp | Leu | Ser | Cys | Asn |
| | | 275 | | | | | 280 | | | | | 285 | | | |
| Arg | Leu | Asn | Arg | Ala | Pro | Gln | Pro | Asp | Glu | Leu | Pro | Glu | Val | Asp | Asn |
| | 290 | | | | | 295 | | | | | 300 | | | | |
| Leu | Thr | Leu | Asp | Gly | Asn | Pro | Phe | Leu | Val | Pro | Gly | Thr | Ala | Leu | Pro |
| 305 | | | | | 310 | | | | | 315 | | | | | 320 |
| His | Glu | Gly | Ser | Met | Asn | Ser | Gly | Val | Val | Pro | Ala | Cys | Ala | Arg | Ser |
| | | | | 325 | | | | | 330 | | | | | 335 | |
| Thr | Leu | Ser | Val | Gly | Val | Ser | Gly | Thr | Leu | Val | Leu |
| | | | 340 | | | | | 345 | | | |

( 2 ) INFORMATION FOR SEQ ID NO:46:

( i ) SEQUENCE CHARACTERISTICS:
        ( A ) LENGTH: 8 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..4
        ( D ) OTHER INFORMATION: /note= "Xaa at position 1 is Asp or
        Glu;Xaa at position 2 is Ala or Ser;Xaa at position 3
        is Asp or Glu;Xaa at position 4 is Pro or Gly"

( i x ) FEATURE:
        ( A ) NAME/KEY: Protein ( B ) LOCATION: 5..8
( D ) OTHER INFORMATION: /note= "Xaa at position 5 is Arg or
Lys;Xaa at position 6 is Gln,Asn or His;Xaa at position
7 is Tyr, Trp or Phe;Xaa at position 8 is Ala or Ser"

( x i ) SEQUENCE DESCRIPTION: SEQ ID NO:46:

Xaa Xaa Xaa Xaa Xaa Xaa Xaa Xaa
1               5

( 2 ) INFORMATION FOR SEQ ID NO:47:

( i ) SEQUENCE CHARACTERISTICS:
        ( A ) LENGTH: 7 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..6
        ( D ) OTHER INFORMATION: /note= "Xaa at position 1 is Asp or
Glu;Xaa at position 2 is Pro or Gly;Xaa at position 3 is
Arg or Lys;Xaa at position 4 is Gln, Asn or His;Xaa at
position 5 is Tyr,Trp or Phe;Xaa at position 6 is Ala
or Ser"

( i x ) FEATURE:
        ( A ) NAME/KEY: Modified-site
        ( B ) LOCATION: 1..7
        ( D ) OTHER INFORMATION: /note= "amino acids 1 and 7 are
linked together by -CO-(CH2)n-S-, wherein n=1 to 3"

( x i ) SEQUENCE DESCRIPTION: SEQ ID NO:47:

Xaa Xaa Xaa Xaa Xaa Xaa Cys
1               5

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Protein
        ( B ) LOCATION: 1..4
        ( D ) OTHER INFORMATION: /note= "Xaa at position 1 is Ala or
Ser;Xaa at position 2 is Asp or Glu;Xaa at position 3
is Pro or Gly;Xaa at position 4 is Arg or Lys"

( i x ) FEATURE:
        ( A ) NAME/KEY: Protein
        ( B ) LOCATION: 5..8
        ( D ) OTHER INFORMATION: /note= "Xaa at position 5 is
Gln,Asn or His;Xaa at position 6 is Tyr, Trp or Phe;Xaa
at 7 is Ala or Ser;Xaa at position 8 is Asp or Glu"

( i x ) FEATURE:
        ( A ) NAME/KEY: Modified-site
        ( B ) LOCATION: 1..9
        ( D ) OTHER INFORMATION: /note= "amino acids 1 and 9 are
linked together by -CO-(CH2)n-S-, wherein n= 1 to 3"

( x i ) SEQUENCE DESCRIPTION: SEQ ID NO:48:

Xaa Xaa Xaa Xaa Xaa Xaa Xaa Xaa Cys
1               5

( 2 ) INFORMATION FOR SEQ ID NO:49:

```
    ( i ) SEQUENCE CHARACTERISTICS:
           ( A ) LENGTH: 11 amino acids
           ( B ) TYPE: amino acid
           ( C ) STRANDEDNESS: unknown
           ( D ) TOPOLOGY: unknown ( i i ) MOLECULE TYPE: protein ( i x ) FEATURE:
           ( A ) NAME/KEY: Protein
           ( B ) LOCATION: 1..5
           ( D ) OTHER INFORMATION: /note= "Xaa at position 1 is Asp or
                  Glu;Xaa at position 2 is Ala or Ser;Xaa at position 3 is
                  Asp or Glu;Xaa at position 4 is Pro or Gly;Xaa at
                  position 5 is Arg or Lys "

( i x ) FEATURE:
           ( A ) NAME/KEY: Protein
           ( B ) LOCATION: 6..10
           ( D ) OTHER INFORMATION: /note= "Xaa at position 6 is Gln,
                  Asn or His;Xaa at position 7 is Tyr, Trp or Phe;Xaa at
                  position 8 is Ala or Ser;Xaa at position 9 is Asp or
                  Glu;Xaa at position 10 is Thr or Ser"

( i x ) FEATURE:
           ( A ) NAME/KEY: Modified-site
           ( B ) LOCATION: 1..11
           ( D ) OTHER INFORMATION: /note= "amino acids 1 and 11 are
                  linked together by -CO-(CH2)n-S-,wherein n = 1 to 3"

( x i ) SEQUENCE DESCRIPTION: SEQ ID NO:49:

Xaa  Xaa  Xaa  Xaa  Xaa  Xaa  Xaa  Xaa  Xaa  Xaa  Cys
    1              5                        10
```